US011620772B2

(12) United States Patent
Rosen et al.

(10) Patent No.: US 11,620,772 B2
(45) Date of Patent: Apr. 4, 2023

(54) SYSTEM AND METHOD FOR AUTOMATED TRANSFORM BY MANIFOLD APPROXIMATION

(71) Applicant: THE GENERAL HOSPITAL CORPORATION, Boston, MA (US)

(72) Inventors: Matthew S. Rosen, Somerville, MA (US); Bo Zhu, Cambridge, MA (US); Bruce R. Rosen, Lexington, MA (US)

(73) Assignee: The General Hospital Corporation, Boston, MA (US)

( * ) Notice: Subject to any disclaimer, the term of this patent is extended or adjusted under 35 U.S.C. 154(b) by 116 days.

(21) Appl. No.: 16/326,910

(22) PCT Filed: Sep. 1, 2017

(86) PCT No.: PCT/US2017/049832
§ 371 (c)(1),
(2) Date: Feb. 20, 2019

(87) PCT Pub. No.: WO2018/045274
PCT Pub. Date: Mar. 8, 2018

(65) Prior Publication Data
US 2019/0213761 A1 Jul. 11, 2019

Related U.S. Application Data

(60) Provisional application No. 62/510,572, filed on May 24, 2017, provisional application No. 62/382,490, filed on Sep. 1, 2016.

(51) Int. Cl.
*G06T 11/00* (2006.01)
*G01R 33/56* (2006.01)
(Continued)

(52) U.S. Cl.
CPC .......... *G06T 11/006* (2013.01); *A61B 5/0035* (2013.01); *A61B 5/0059* (2013.01);
(Continued)

(58) Field of Classification Search
CPC ... G06T 11/006; G06T 2210/41; G01R 33/12; G01R 33/4818; G01R 33/5608;
(Continued)

(56) References Cited

U.S. PATENT DOCUMENTS 6,462,342 B1 * 10/2002 Stearns ................. G06T 11/005
250/363.04
6,710,686 B2 3/2004 Mertelmeier et al.
(Continued)

FOREIGN PATENT DOCUMENTS

CN 1857161 A 11/2006
CN 101785670 A 7/2010
(Continued)

OTHER PUBLICATIONS

Han PRMLSS 2015 deconvolutions in Convolutional Neural Networks—Downloaded on May 8, 2016—Internet access: http://www.aisociety.kr/prml/PRMLSS_2015_deconvolution.pdf (Year: 2015).*
(Continued)

*Primary Examiner* — Keith M Raymond
*Assistant Examiner* — Patrick M Mehl
(74) *Attorney, Agent, or Firm* — Quarles & Brady LLP

(57) ABSTRACT

A system may transform sensor data from a sensor domain to an image domain using data-driven manifold learning techniques which may, for example, be implemented using neural networks. The sensor data may be generated by an image sensor, which may be part of an imaging system. Fully connected layers of a neural network in the system may be applied to the sensor data to apply an activation function to the sensor data. The activation function may be
(Continued)

a hyperbolic tangent activation function. Convolutional layers may then be applied that convolve the output of the fully connected layers for high level feature extraction. An output layer may be applied to the output of the convolutional layers to deconvolve the output and produce image data in the image domain.

30 Claims, 11 Drawing Sheets

(51) Int. Cl.
  *G06N 3/08*   (2006.01)
  *G01R 33/12*   (2006.01)
  *G06K 9/62*   (2022.01)
  *G06N 3/04*   (2006.01)
  *G16H 30/40*   (2018.01)
  *A61B 5/00*   (2006.01)
  *A61B 5/055*   (2006.01)
  *A61B 6/03*   (2006.01)
  *A61B 6/00*   (2006.01)
  *A61B 8/00*   (2006.01)
  *A61B 8/08*   (2006.01)
  *G01R 33/48*   (2006.01)

(52) U.S. Cl.
  CPC ............ *A61B 5/055* (2013.01); *A61B 5/7267* (2013.01); *A61B 5/7425* (2013.01); *A61B 6/032* (2013.01); *A61B 6/037* (2013.01); *A61B 6/463* (2013.01); *A61B 6/5247* (2013.01); *A61B 8/463* (2013.01); *A61B 8/5261* (2013.01); *G01R 33/12* (2013.01); *G01R 33/4818* (2013.01); *G01R 33/5608* (2013.01); *G06K 9/623* (2013.01); *G06K 9/6274* (2013.01); *G06N 3/0454* (2013.01); *G06N 3/08* (2013.01); *G16H 30/40* (2018.01); *G01R 33/4824* (2013.01); *G06T 2210/41* (2013.01); *G06V 2201/03* (2022.01)

(58) Field of Classification Search
  CPC .. G01R 33/4824; G06K 9/6274; G06K 9/623; G06K 2209/05; G06N 3/0454; G06N 3/08; G16H 30/40; A61B 5/0035; A61B 5/0059; A61B 5/055; A61B 5/7267; A61B 5/7425; A61B 6/032; A61B 6/037; A61B 6/463; A61B 6/5247; A61B 8/463; A61B 8/5261; A61B 6/5205; A61B 6/5207
  See application file for complete search history.

(56) References Cited

U.S. PATENT DOCUMENTS

| | | | |
|---|---|---|---|
| 7,646,924 | B2 | 1/2010 | Donoho |
| 8,374,413 | B2 | 2/2013 | Chen |
| 2007/0288410 | A1* | 12/2007 | Tomkins ............... G06N 3/086 706/42 |
| 2008/0100292 | A1 | 5/2008 | Hancu |
| 2009/0096447 | A1 | 4/2009 | Prance et al. |
| 2013/0211238 | A1* | 8/2013 | DeCharms ........... A61B 5/0042 600/418 |
| 2014/0378815 | A1 | 12/2014 | Huang et al. |
| 2015/0198684 | A1 | 7/2015 | Basha et al. |
| 2016/0072531 | A1* | 3/2016 | Abrishamkar ........... G06N 3/04 455/65 |

FOREIGN PATENT DOCUMENTS

| | | |
|---|---|---|
| CN | 103646410 A | 3/2014 |
| CN | 103679654 A | 3/2014 |
| CN | 105872046 A | 8/2016 |
| WO | 2017166586 A1 | 10/2017 |

OTHER PUBLICATIONS

Wang et al. 2016 IEEE 13th Internal. Symp. Biomed. Imag. 514-517; (Year: 2016).*
Wang 1998 Int. J. Imaging Syst. Technol. 9:381-387; Pub.Date 1998) (Year: 1998).*
Batenburg et al. 2006 IWCIA 2006 LNCS 4040: 389-403 (Year: 2006).*
Seyyedsalehi et al. 2014 Neural Process Lett. 40:191-209 (Year: 2014).*
Abadi et al., TensorFlow: Large-Scale Machine Learning on Heterogeneous Distributed Systems, Preliminary White Paper, Nov. 9, 2015, arXiv:1603.04467, 2016, pp. 1-19.
Anderes et al., A General Spline Representation for Nonparametric and Semiparametric Density Estimates Using Diffeomorphisms, arXiv:1205.5314, 2012, 21 pages.
Arridge et al., Image Reconstruction in Optical Tomography, Philosophical Transactions of the Royal Society of London, Series B: Biological Sciences, 1997, 352(1354):717-726.
Beister et al., Iterative Reconstruction Methods in X-ray CT, Physica Medica, 2012, 28(2):94-108.
Bengio et al., Representation Learning: A Review and New Perspectives, IEEE Transactions on Pattern Analysis and Machine Intelligence, 2013, 35(8): 1798-1828.
Bernstein et al., Manifold Learning in Regression Tasks, In Statistical Learning and Data Sciences, SLDS 2015, Lecture Notes in Computer Science, vol. 9047, pp. 414-423.
Daigle et al., Characterization Results of EMCCDs for Extreme Low-Light Imaging, Proc SPIE 8453, High Energy, Optical, and Infrared Detectors for Astronomy V, 2012, p. 845303, 9 pages.
Deng et al., ImageNet: A Large-Scale Hierarchical Image Database, 2009 IEEE Conference on Computer Vision and Pattern Recognition, 2009, pp. 248-255.
Fan et al., MGH-USC Human Connectome Project Datasets with Ultra-High b-Value Diffusion MRI, Neuroimage, 2016, 124:1108-1114.
Fessler et al., Nonuniform Fast Fourier Transforms Using Min-Max Interpolation, IEEE Transactions on Signal Processing, 2003, 51(2):560-574.
Fishbaugh et al., Geodesic Image Regression with a Sparse Parameterization of Diffeomorphisms, Geometric Science of Information, 2013, 8085:95-102.
Getis, Spatial Autocorrelation, Handbook of Applied Spatial Analysis, 2010, pp. 255-278.
Gilbert et al., The Neural Basis of Perceptual Learning, Neuron, 2001, 31(5):681-697.
Girard et al., Sparse Representations and Convex Optimization as Tools for LOFAR Radio Interferometric Imaging, Journal of Instrumentation, 2015, 10(08):C08013.
Gold et al., Signal But Not Noise Changes with Perceptual Learning, Nature, 1999, 402(6758):176-178.
Gull et al., Image Reconstruction From Incomplete and Noisy Data, Nature, 1978, 272(5655):686-690.
Hansen et al., AIR Tools—A Matlab Package of Algebraic Iterative Reconstruction Methods, Journal of Computational and Applied Mathematics, 2012, 236(8):2167-2178.
Hinton et al., Deep Neural Networks for Acoustic Modeling in Speech Recognition: The Shared Views of Four Research Groups, IEEE Signal Processing Magazine, 2012, pp. 82-97.
Hornik et al., Multilayer Feedforward Networks are Universal Approximators, Neural Networks, 1989, 2(5):359-366.
Hornik, Approximation Capabilities of Multilayer Feedforward Networks, Neural Networks, 1991, 4(2):251-257.
Hui et al., MRI Reconstruction From Truncated Data Using a Complex Domain Backpropagation Neural Network, IEEE Pacific

(56) References Cited

OTHER PUBLICATIONS

Rim Conference on Communications, Computers, and Signal Processing Proceedings, 1995, pp. 513-516.

Karras et al., Neural Network Reconstruction of MR Images from Noisy and Sparse k-space Samples, WCC 2000-ICSP, 5th International Conference on Signal Processing Proceedings, 16th World Computer Congress 2000, vol. 3, pp. 2115-2118.

Kim et al., Simple Analytic Variable Density Spiral Design, Magnetic Resonance in Medicine, 2003, 50(1):214-219.

Kinahan et al., Chapter 20—Analytic Image Reconstruction Methods, Emission Tomography: The Fundamentals of PET and SPECT, 2004, pp. 421-442.

Krizhevsky et al., ImageNet Classification with Deep Convolutional Neural Networks, Advances in Neural Information Processing Systems, 2012, 25:1097-1105.

Kubo et al., Radiation Dose Reduction in Chest CT: A Review, American Journal of Roentgenology, 2008, 190 (2):335-343.

Lebed et al., Rapid Volumetric OCT Image Acquisition Using Compressive Sampling, Optics Express, 2010, 18(20):21003-21012.

Lu et al., Visual Perceptual Learning, Neurobiology of Learning and Memory, 2011, 95(2):145-151.

Lustig et al., Sparse MRI: The Application of Compressed Sensing for Rapid MR Imaging, Magnetic Resonance in Medicine, 2007, 58:1182-1195.

Lustig et al., SPIRiT: Iterative Self-Consistent Parallel Imaging Reconstruction from Arbitrary k-Space, Magnetic Resonance in Medicine, 2010, 64(2):457-471.

Makhzani et al., Winner-Take-All Autoencoders, Proceedings of the 28th International Conference on Neural Information Processing Systems, 2015, 2:2791-2799.

Nair et al., Rectified Linear Units Improve Restricted Boltzmann Machines, Icml, 2010, 8 pages.

Poggio et al., Networks for Approximation and Learning, Proceedings of the IEEE, 1990, 78(9):1481-1497.

Pruessmann et al., Advances in Sensitivity Encoding With Arbitrary k-Space Trajectories, Magnetic Resonance in Medicine, 2001, 46:638-651.

Reczko et al., Improved MR Image Reconstruction From Sparsely Sampled Scans based on Neural Networks, Pattern Recognition Letters, 2001, 22(1):35-46.

Sinha et al., Parallel Magnetic Resonance Imaging Using Neural Networks, In 2007 IEEE International Conference on Image Processing, vol. 3, pp. 149-152.

Sinha et al., Composite MR Image Reconstruction and Unaliasing for General Trajectories Using Neural Networks, Magnetic Resonance Imaging, 2010, 28(10):1468-1484.

Smith et al., A Data Extrapolation Algorithm Using a Complex Domain Neural Network, IEEE Transactions on Circuits and Systems II: Analog and Digital Signal Processing, 1997, 44(2):143 147.

Uecker et al., Berkeley Advanced Reconstruction Toolbox, Proc. Intl. Soc. Mag. Reson. Med, 2015, 23:2486.

Van Der Maaten et al., Visualizing Data Using t-SNE, Journal of Machine Learning Research, 2008, 9(11) 2579-2605.

Vincent et al., Extracting and Composing Robust Features with Denoising Autoencoders, Proceedings of the 25th International Conference on Machine Learning, 2008, pp. 1096-1103.

Virtue et al., The Empirical Effect of Gaussian Noise in Undersampled MRI Reconstruction, Tomography, 2017, 3 (4):211-221.

Wright et al., Sparse Representation for Computer Vision and Pattern Recognition, Proceedings of the IEEE, 2010, 98(6):1031-1044.

Yan et al., Data Truncation Artifact Reduction in MR Imaging Using a Multilayer Neural Network, IEEE Transactions on Medical Imaging, 1993, 12(1):73-77.

Yang et al., Mean Square Optimal NUFFT Approximation for Efficient Non-Cartesian MRI Reconstruction, Journal of Magnetic Resonance, 2014, 242:126-135.

Yu et al., Improved Local Coordinate Coding Using Local Tangents, ICML, 2010, 8 pages.

Zhang et al., Bayesian Estimation of Regularization and Atlas Building in Diffeomorphic Image Registration, Information Processing in Medical Imaging, 2013, 23:37-48.

Vincent et al., Extracting and Composing Robust Features with Denoising Autoencoders, Proceedings of the 25th International Conference on Machine Learning, 2008, 8 pages, Helsinki, Finland.

Candes et al., Robust Uncertainty Principles: Exact Signal Reconstruction from Highly Incomplete Frequency Infomnation, IEEE Transactions on Information Theory, 2006, 52(2):489-509.

Donoho, Compressed Sensing, IEEE Transactions on Information Theory, 2006, 52(4):1289-1306.

PCT International Search Report and Written Opinion, PCT/US2017/049832, dated Nov. 8, 2017, 9 pages.

Cierniak et al., A New Approach to Image Reconstruction from Projections Using a Recurrent Neural Network, International Journal of Applied Mathematics & Computer Science, 2008, 18(2):147-157.

Zhu et al., Image Reconstruction by Domain Transform Manifold Learning, Nature, 2018, 555(7697):487-492.

\* cited by examiner

SYSTEM AND METHOD FOR AUTOMATED TRANSFORM BY MANIFOLD APPROXIMATION

CROSS-REFERENCE TO RELATED APPLICATIONS

This application represents the National Stage Entry of PCT International Application No. PCT/US2017/049832 filed Sep. 1, 2017, which is based on, claims priority to, and incorporates herein by reference in their entirety U.S. Provisional Application Ser. No. 62/382,490, filed Sep. 1, 2016, and U.S. Provisional Application Ser. No. 62/510,572, filed May 24, 2017.

STATEMENT REGARDING FEDERALLY SPONSORED RESEARCH

N/A

BACKGROUND

The present disclosure relates generally to imaging and, more particularly, to system and methods for reconstructing images from acquired data.

Imaging is important to a wide range of industries and activities. From space exploration to oil exploration, imaging plays a key role in these endeavors. The modalities available for imaging are at least as diverse as the industries that employ them. For example, in the medical industry alone, a staggeringly large number of imaging modalities are employed in regular, clinical medicine. For example, to name but a few, magnetic resonance imaging (MRI), computed tomography (CT) imaging, emission tomography imaging (including modalities such as positron emission tomography and single photon emission computed tomography), optical, x-ray fluoroscopy, and many, many others are utilized each day in modern medicine.

Regardless of the modality employed or the industry/application, reconstruction is a key process in any imaging process. In some settings, image reconstruction may be quite rudimentary or well settled. For example, image reconstruction for x-ray fluoroscopy generally includes translating attenuation values into contrast values in the digital image. Other modalities require much more complex reconstruction techniques.

In a computed tomography system, an x-ray source projects a fan-shaped beam which is collimated to lie within an x-y plane of a Cartesian coordinate system, termed the "image plane." The x-ray beam passes through the object being imaged, such as a medical patient, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce what is called the "transmission profile," or "attenuation profile" or "projection." In x-ray fluoroscopy, this 2D projection is translated into a single image.

The source and detector array in a conventional CT system are rotated on a gantry within the imaging plane and around the object so that the angle at which the x-ray beam intersects the object constantly changes. The transmission profile from the detector array at a given angle is referred to as a "view" and a "scan" of the object comprises a set of views made at different angular orientations during one revolution of the x-ray source and detector. In a 2D scan, data is processed to construct an image that corresponds to a two dimensional slice taken through the object. The prevailing method for reconstructing an image from 2D data is referred to in the art as the filtered backprojection technique. This image reconstruction process converts the attenuation measurements acquired during a scan into integers called "CT numbers" or "Hounsfield units", which are used to control the brightness of a corresponding pixel on a display.

The filtered backprojection image reconstruction method is the most common technique used to reconstruct CT images from acquired transmission profiles. As shown in FIG. 1 each acquired x-ray transmission profile 100 is backprojected onto the field of view (FOV) 102 by projecting each ray sum 104 in the profile 100 through the FOV 102 along the same ray path that produced the ray sum 104 as indicated by arrows 106. In projecting each ray sum 104 in the FOV 102 we have no a priori knowledge of the subject and the assumption is made that the x-ray attenuation in the FOV 102 is homogeneous and that the ray sum should be distributed equally in each pixel through which the ray path passes. For example, a ray path 108 is illustrated in FIG. 1 for a single ray sum 104 in one transmission profile 100 and it passes through N pixels in the FOV 102. The attenuation value, P, of this ray sum 104 is divided up equally between these N pixels:

$$\mu_n = \frac{(P \times 1)}{N}$$

where $\mu_n$ is the attenuation value distributed to the $n^{th}$ pixel in a ray path having N pixels.

Clearly, the assumption that attenuation in the FOV 102 is homogeneous is not correct. However, as is well known in the art, if certain corrections are made to each transmission profile 100 and a sufficient number of profiles are acquired at a corresponding number of projection angles, the errors caused by this faulty assumption are minimized and image artifacts are suppressed. In a typical filtered backprojection method of image reconstruction, anywhere from 400 to 1000 views are typically required to adequately suppress image artifacts in a 2D CT image.

Magnetic resonance imaging (MRI) uses the nuclear magnetic resonance (NMR) phenomenon to produce images. When a substance such as human tissue is subjected to a uniform magnetic field (polarizing field $B_0$), the individual magnetic moments of the spins in the tissue tend to align with this polarizing field, If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_{xy}$. A signal is emitted by the excited spins, and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals, or k-space (e.g., frequency domain) samples, are digitized and processed to reconstruct the image using one of many well-known reconstruction techniques.

Most commonly, when the k-space data is acquired using Cartesian sampling, the reconstruction of the data from k-space to the image space is achieved using a Fourier transform or any of a variety of reconstruction techniques that utilize a Fourier transform. Such a k-space sampling is illustrated in FIG. 2A. There are many, many variations on techniques for using the Fourier transform as part of a reconstruction process for k-space data sampled using a Cartesian or similar sampling strategy.

Projection reconstruction methods have been known since the inception of magnetic resonance imaging. Rather than sampling k-space in a rectilinear, or Cartesian, scan pattern as is done in Fourier imaging and shown in FIG. 2A, projection reconstruction methods sample k-space data with a series of views that sample radial lines extending outward from the center of k-space as shown in FIG. 2B. The number of views needed to sample k-space determines the length of the scan and if an insufficient number of views are acquired, streak artifacts are produced in the reconstructed image.

Two example methods used to reconstruct images from an acquired set of projection views are described, for example, in U.S. Pat. No. 6,710,686. In MRI the most common method is to regrid the k-space samples (e.g., NMR data) from their locations on the radial sampling trajectories to a Cartesian grid. The image is then reconstructed by performing a 2D or 3D Fourier transformation of the regridded k-space samples. The second method for reconstructing an MR image is to transform the radial k-space projection views to Radon space by first Fourier transforming each projection view. An image is reconstructed from these signal projections by filtering and backprojecting them into the field of view (FOV). As is well known in the art, if the acquired signal projections are insufficient in number to satisfy the Nyquist sampling theorem, streak artifacts are produced in the reconstructed image.

Depending on the technique used, many MR scans currently used to produce medical images require many minutes to acquire the necessary data. The reduction of this scan time is an important consideration, since reduced scan time increases patient throughout, improves patient comfort, and improves image quality by reducing motion artifacts. Many different strategies have been developed to shorten the scan time.

One such strategy is referred to generally as "parallel imaging". Parallel imaging techniques use spatial information from arrays of RF receiver coils to substitute for the encoding that would otherwise have to be obtained in a sequential fashion using RF pulses and field gradients (such as phase and frequency encoding). Each of the spatially independent receiver coils of the array carries certain spatial information and has a different sensitivity profile. This information is utilized in order to achieve a complete location encoding of the received MR signals by a combination of the simultaneously acquired data received from the separate coils. Specifically, parallel imaging techniques undersample k-space by reducing the number of acquired phase-encoded k-space sampling lines while keeping the maximal extent covered in k-space fixed. The combination of the separate MR signals produced by the separate receiver coils enables a reduction of the acquisition time required for an image (in comparison to conventional k-space data acquisition) by a factor that in the most favorable case equals the number of the receiver coils. Thus the use of multiple receiver coils acts to multiply imaging speed, without increasing gradient switching rates or RF power.

Two categories of such parallel imaging techniques that have been developed and applied to in vivo imaging are SENSE (SENSitivity Encoding) and SMASH (SiMultaneous Acquisition of Spatial Harmonics). With SENSE, the undersampled k-space data is first Fourier transformed to produce an aliased image from each coil, and then the aliased image signals are unfolded by a linear transformation of the superimposed pixel values. With SMASH, the omitted k-space lines are filled in or reconstructed prior to Fourier transformation, by constructing a weighted combination of neighboring lines acquired by the different receiver coils. SMASH requires that the spatial sensitivity of the coils be determined, and one way to do so is by "autocalibration" that entails the use of variable density k-space sampling.

The data acquisition methods are significantly different in the above exemplary imaging modalities. Namely, k-space is sampled to measure Fourier coefficients in MR data acquisitions, while line integrals are measured in x-ray CT data acquisitions. Despite this, the challenge in image reconstruction for both modalities, as well as many other imaging modalities, is common: reconstructing a high quality image.

According to standard image reconstruction theories, in order to reconstruct an image without aliasing artifacts, the sampling rate employed to acquire image data must satisfy the so-called Nyquist criterion, which is set forth in the Nyquist-Shannon sampling theorem. Moreover, in standard image reconstruction theories, no specific prior information about the image is needed. On the other hand, when some prior information about the desired or target image is available and appropriately incorporated into the image reconstruction procedure, an image can be accurately reconstructed even if the Nyquist criterion is violated. For example, if one knows a desired, target image is circularly symmetric and spatially uniform, only one view of parallel-beam projections (i.e., one projection view) is needed to accurately reconstruct the linear attenuation coefficient of the object. As another example, if one knows that a desired, target image consists of only a single point, then only two orthogonal projections that intersect at said point are needed to accurately reconstruct the image point. Thus, if prior information is known about the desired target image, such as if the desired target image is a set of sparsely distributed points, it can be reconstructed from a set of data that was acquired in a manner that does not satisfy the Nyquist criterion. Put more generally, knowledge about the sparsity of the desired target image can be employed to relax the Nyquist criterion; however, it is a highly nontrivial task to generalize these arguments to formulate a rigorous image reconstruction theory.

The Nyquist criterion serves as one of the paramount foundations of the field of information science. However, it also plays a pivotal role in modern medical imaging modalities such as MRI and x-ray CT imaging. When the number of data samples acquired by an imaging system is less than the requirement imposed by the Nyquist criterion, artifacts appear in the reconstructed images. In general, such image artifacts include aliasing and streaking artifacts. In practice, the Nyquist criterion is often violated, whether intentionally or through unavoidable circumstances. For example, in order to shorten the data acquisition time in a time-resolved MR angiography study, undersampled projection reconstruction, or radial, acquisition methods are often intentionally introduced.

In contrast, undersampling is inevitable in four-dimensional cone beam CT (4D CBCT), such as when utilized in image-guided radiation therapy (IGRT). For example, in the case of IGRT, cone beam projection data are acquired over 10-15 respiratory cycles during a 60 second gantry rotation time. The acquired data is then retrospectively gated into 8-10 phases by synchronizing the respiratory signals with the data acquisition. After the respiratory gating, less than 100 cone beam projections are typically available to reconstruct images for each respiratory phase. Consequently, streaking artifacts are rampant in the reconstructed images for each respiratory phase. These undersampling artifacts pose a major challenge in 4D CBCT and limit the use of 4D CBCT in clinical practice.

Some image reconstruction methods have attempted to use prior or other information to overcome challenges to producing high-quality images. For example, one method called highly constrained backprojection (HYPR) has been developed in which quality images can be reconstructed from far fewer projection signal profiles when a priori knowledge of the signal information is used in the reconstruction process. For example, signal information in an angiographic study may be known to include structures such as blood vessels. That being the case, when a backprojection path passes through these structures a more accurate distribution of a signal sample in each pixel can be achieved by weighting the distribution as a function of the known signal information at that pixel location. In HYPR, for a backprojection path having N pixels the highly constrained backprojection may be expressed as follows:

$$S_n = \frac{(P \times C_n)}{\sum_{n=1}^{N} C_n},$$

where $S_n$ is the backprojected signal magnitude at a pixel n in an image frame being reconstructed, P is the signal sample value in the projection profile being backprojected, and $C_n$ is the signal value of an a priori composite image at the $n^{th}$ pixel along the backprojection path. The composite image is reconstructed from data acquired during the scan, and may include that used to reconstruct the given image frame as well as other acquired image data that depicts the structures in the field of view. The numerator in the equation above, $(P \times C_n)$, weights each pixel using the corresponding signal value in the composite image and the denominator, $$\sum_{n=1}^{N} C_n,$$

normalizes the value so that all backprojected signal samples reflect the projection sums for the image frame and are not multiplied by the sum of the composite image.

Also recently, a mathematical framework for image reconstruction termed "compressed sensing" (CS) has been used for some image reconstruction techniques. In compressed sensing, only a small set of linear projections of a sparse image are required to reconstruct a quality image. The theory of CS is described in E. Candès, J. Romberg, and T. Tao, "Robust uncertainty principles: Exact signal reconstruction from highly incomplete frequency information," *IEEE Transactions on Information Theory* 2006; 52:489-509, and D. Donoho, "Compressed sensing," *IEEE Transactions on Information Theory* 2006; 52:1289-1306, and is disclosed, for example, in U.S. Pat. No. 7,646,924. Some techniques have leveraged the signal processing concept of CS to perform reconstruction of computed tomography data. One such example is provided in U.S. Pat. No. 8,374,413, which describes the so-called prior image constrained compressed sensing reconstruction (PICCS) technique.

Regardless of the imaging modality or the data-type acquired, all reconstruction techniques are fundamentally based on a few principles. First, a known data sampling is performed to yield a set of data of known characteristics. Then, based on the known data sampling technique and the known characteristics of the data set, an appropriate reconstruction technique is applied that will transform the raw set of data into an image. Thus, a known reconstruction technique matched to the underlying data is applied that serves to transform the raw data from a first domain in which it was acquired to a second domain where it can be understood as an image.

For example, in CT, the data is acquired as Hounsfield units that are transformed using filtered backprojection or another technique into pixels with associated contrast values in an image. In MR, the data is acquired as k-space or frequency domain data that is transformed using, typically a type of Fourier transform, into the image domain (e.g., a spatial domain in which the arrangement and relationship among different pixel values are expressed) to generate an image. Other imaging modalities follow this exact or similar process. For example, PET imaging uses the filtered backprojection technique.

Despite the success of this paradigm in medical and non-medical imaging applications, they suffer from regular and extensive shortcomings. Case in point, the Nyquist criterion is a fundamental tenant of imaging that, when not observed, often requires extensive efforts to buttress the applicable reconstruction technique with additional compensations to overcome the fact that the resulting images, without such compensation, would suffer from artifacts that reduce the value of the images. Thus, in the patent literature alone, there are thousands of examples of small changes, additions, or variations on the fundamental reconstruction techniques.

It would be desirable to have a system and method that can transform raw data into an image and, thereby, serve as a reconstruction technique, but without the need for the reconstruction technique being predesigned to compensate for anticipated data acquisition characteristics, including shortcomings in the data (such as undersampling). Furthermore, it would be desirable if the reconstruction technique could provide feedback that informs the data acquisition techniques that can be used in the future. That is, it would be desirable that the reconstruction process not be dictated by the data acquisition process, but that data reconstruction be performed irrespective of data acquisition and, instead, serve to inform future data acquisitions to further improve reconstructed images.

SUMMARY OF THE DISCLOSURE

The present disclosure provides systems and methods for generating images from sensor data. As will be described, the systems and methods provide greater flexibility and improved results than traditional image-creation systems and methods.

In accordance with one aspect of the disclosure, a medical imaging system may include an image sensor, a processor, and a display. The image sensor may acquire image data from a patient, and this image data may be in a sensor domain. The processor may receive the sensor data from the image sensor and may transform the sensor data from the sensor domain to an image domain using a neural network to produce an image of the patient. The display may display the image of the patient.

In some embodiments, the image sensor may include at least one of a radio frequency (RF) system of a magnetic resonance imaging (MRI) system where the sensor data includes magnetic resonance data, an x-ray detector of a computed tomography (CT) system where the sensor data includes x-ray attenuation data; a gamma ray detector of an emission tomography system where the sensor data includes emission tomography data, an ultrasound transducer of an ultrasound system where the sensor data includes ultrasound data, and an optical sensor of an optical imaging system where the sensor data includes optical imaging data.

In accordance with another aspect of the disclosure, a system may include an input that receives sensor data in a sensor domain from an image sensor that generates the sensor data, wherein the sensor data corresponds to a captured image, and a processor that receives the sensor data from the image sensor and transforms the sensor data from the sensor domain to an image domain using a neural network.

In some embodiments, the processor may transform the sensor data from the sensor domain to the image domain using the neural network by applying the multiple fully connected layers of the neural network to the sensor data to produce a matrix. Each fully connected layer represents a matrix multiplication followed by an activation function. The multiple fully connected layers may include an input layer that separates real components of the sensor data from imaginary components of the sensor data and that concatenates the real components and the imaginary components to produce an input vector, a first hidden layer that is applied to the input vector, and a second hidden layer layer that produces the matrix from the first hidden layer. The matrix may have dimensions corresponding to dimensions of the sensor data.

In some embodiments, the non-linear activation function may be a hyperbolic tangent activation function.

In some embodiments, the processor may further transform the sensor data from the sensor domain to the image domain using the neural network by applying, with multiple convolutional layers of the neural network, a predetermined number of convolutional filters to the matrix, and by applying, with a deconvolutional layer of the neural network, a predetermined number of deconvolutional filters to a convolutional layer of the multiple convolutional layers to produce image data in the image domain that corresponds to the captured image.

In some embodiments, the image sensor may include at least one of a radio frequency (RF) system of a magnetic resonance imaging (MRI) system where the sensor data includes magnetic resonance data, an x-ray detector of a computed tomography (CT) system where the sensor data includes x-ray attenuation data; a gamma ray detector of an emission tomography system where the sensor data includes emission tomography data, an ultrasound transducer of an ultrasound system where the sensor data includes ultrasound data, and an optical sensor of an optical imaging system where the sensor data includes optical imaging data.

In accordance with yet another aspect of the disclosure, a method may include generating sensor data in a sensor domain with an image sensor, receiving the sensor data from the image sensor with a processor, and executing, with the processor, instructions for transforming the sensor data from a sensor domain to an image domain using a neural network to produce a captured image to which the sensor data corresponds.

In some embodiments, executing instructions for transforming the sensor data from the sensor domain to the image domain using the neural network includes executing instructions for processing the sensor data with the multiple fully connected layers of the neural network to produce a matrix. Each fully connected layer may represent a matrix multiplication followed by an activation function. Applying the neural network to the sensor data to produce the matrix may include separating, at an input layer of the plurality of fully connected layers, real components of the sensor data from imaginary components of the sensor data, concatenating, at the input layer, the real components and the imaginary components to produce an input vector, applying a first hidden layer of the multiple fully connected layers to the input vector, and applying a second hidden layer of the plurality of fully connected layers to produce the matrix from the first hidden layer. The matrix may have dimensions corresponding to dimensions of the sensor data.

In some embodiments, the non-linear activation function may be a hyperbolic tangent activation function.

In some embodiments, executing instructions for transforming the sensor data from the sensor domain to the image domain using the neural network may further include applying, with multiple convolutional layers of the neural network, a predetermined number of convolutional filters to the matrix, and applying, with a deconvolutional layer of the neural network, a predetermined number of deconvolutional filters to a convolutional layer of the multiple convolutional layers to produce image data in the image domain that corresponds to the captured image.

In some embodiments, generating the sensor data may include applying, with a magnetic resonance imaging system, a magnetic resonance pulse sequence to a sample, detecting, with the magnetic resonance imaging system, responsive magnetic resonance signals generated by the sample in response to the magnetic resonance pulse sequence, and sampling the responsive magnetic resonance signals to generate the sensor data.

In accordance with yet another aspect of the disclosure, a system may include a processor that may execute instructions for transforming data from a first domain to a second domain by processing the data using a trained neural network. In some embodiments, processing the data using the trained neural network may include applying the multiple fully connected layers of the neural network to the sensor data to produce a matrix. The multiple fully connected layers may include an input layer that separates real components of the data from imaginary components of the data and that concatenates the real components and the imaginary components to produce an input vector, a first hidden layer that operates on the input vector, and a second hidden layer that produces the matrix from the first hidden layer. The matrix may have dimensions corresponding to dimensions of the data.

In some embodiments, the non-linear activation function may be a hyperbolic tangent activation function.

In some embodiments, processing the data using the trained neural network may further include applying, with multiple convolutional layers of the neural network, a predetermined number of convolutional filters to the matrix, and applying, with a deconvolutional layer of the neural network, a predetermined number of deconvolutional filters to a convolutional layer of the multiple convolutional layers to produce transformed data in the second domain.

The foregoing and other aspects and advantages of the invention will appear from the following description. In the description, reference is made to the accompanying drawings which form a part hereof, and in which there is shown by way of illustration a preferred embodiment of the invention. Such an embodiment does not necessarily represent the full scope of the invention, however, and reference is made therefore to the claims and herein for interpreting the scope of the invention.

DETAILED DESCRIPTION

Figure 1:
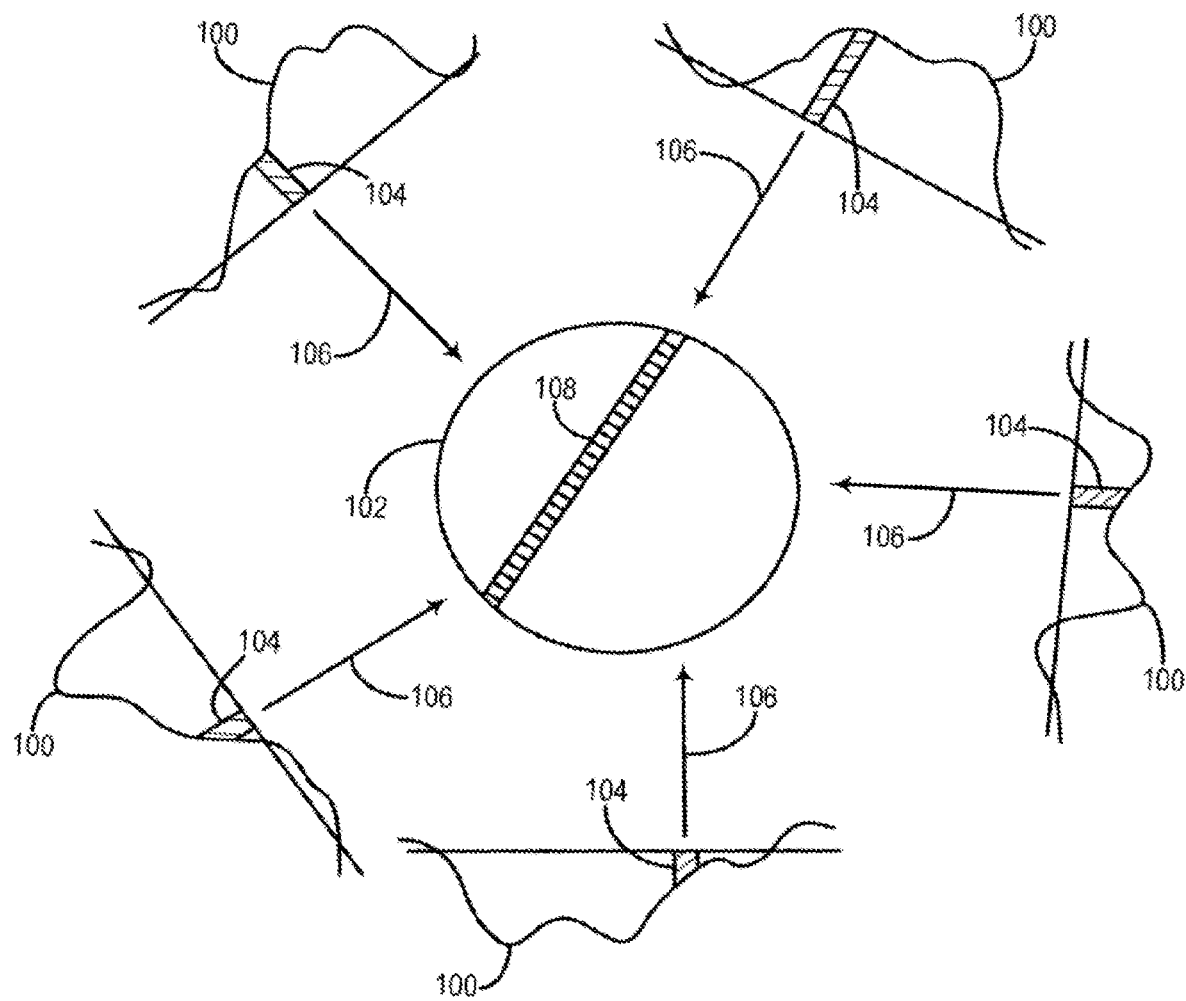
FIG. 1 shows a diagram illustrating filtered backprojection image reconstruction using x-ray transmission profiles.
Figure 2A:
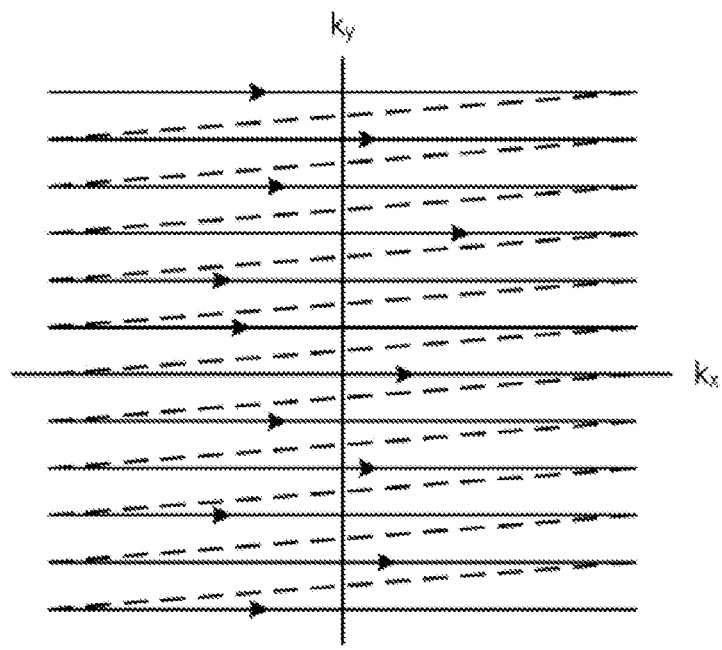
FIG. 2A shows a graph illustrating a Fourier imaging scan pattern that may be used to reconstruct k-space data.
Figure 2B:
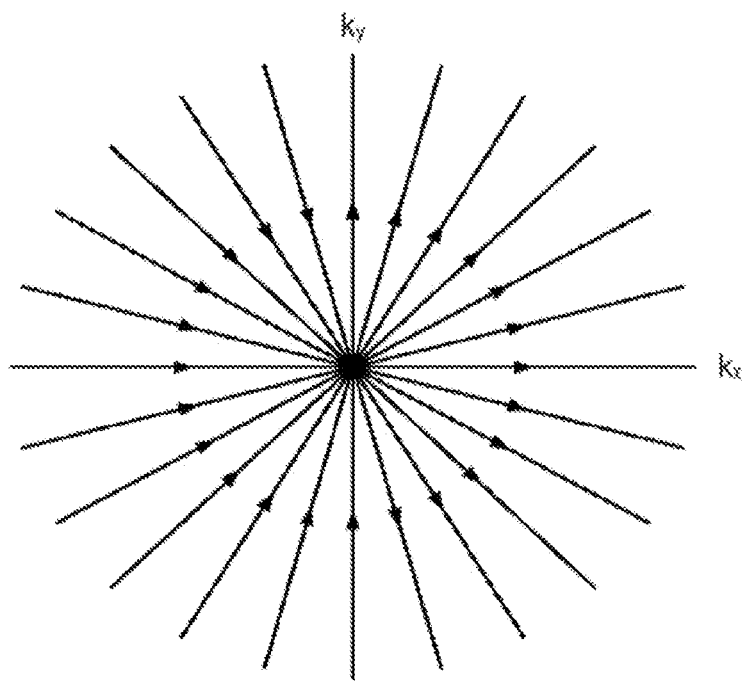
FIG. 2B shows a graph illustrating a projection reconstruction method that may sample k-space data as radial lines extending outward from the center of k-space.

The systems and methods of the present invention can be utilized with a wide variety of data and systems and methods for acquiring and processing data. Some non-limiting examples of imaging systems follow hereafter. However, the systems and methods of the present disclosure are not limited to these modalities or imaging.

As will be described, in one aspect, the present disclosure provides systems and methods for transforming data sets acquired in a first domain into a data set in a second domain using aggregated preferred results in the second domain as a guide for informing the domain transform or reconstruction process. This stands in contrast to traditional domain transform or reconstruction techniques that dictate the way in which the data must be acquired in the first domain so that the domain transform or reconstruction technique can deliver results in the second domain that are desirable. That is, in the case of projections acquired through k-space in MRI, one typically regrids the data to allow a Fourier transform to be performed. In this way, the preconception of the data by the reconstruction technique necessitates that the data be presented (in both form and substance—such as sampling density) in a predetermined manner that will yield desirable images when transformed to the image domain. The present disclosure, provides systems and methods that are not limited in this manner. A framework is provided that can be leveraged to create images or transform data from one domain to another without a preconceived constraint on the data acquired or to be acquired.

For example, a data-driven manifold learning construct can be used as a generalized image reconstruction technique to transform raw sensor to another domain or, in the case of imaging, transform image data into images, without human-devised, acquisition-specific mathematical transforms. In a non-limiting context, this construct or framework may be referred to herein as AUTOMAP (AUtomated TransfOrm by Manifold Approximation) or a deep reconstruction network (DRN).

By not constraining the image reconstruction or domain transfer problem to human-devised, acquisition-specific transforms, new signal domains beyond conventional representations (e.g. k-space/fourier space, O-space, Radon) can be used acquire data. Reinforcement learning can be used to automatically program novel methods for data acquisition. As one non-limiting example, AUTOMAP can be used to design new pulse sequences for MRI. Likewise, the data acquisition itself need not be constrained to known domains. The automated acquisition and automated reconstruction stages can be trained in tandem to produce optimal imaging protocols and resultant images.

Thus, the systems and methods provided herein, may be used in any of a variety of setting where one looks to transform data from one domain to another domain and/or develop and devise data acquisition strategies that yield improved results by analyzing the desired ends to the data acquisition. For example, beyond the non-limiting examples provided herein, the systems and methods of the present disclosure can be extended to other imaging modalities, such as optical (for example, optical coherence tomography, speckle imaging, and the like) and even non-imaging applications, such as general data processing.

Furthermore, the systems and methods provided herein are not limited to applications where a domain transform is necessary or advantageous to yield an image or improved image. This and other points will be made clear with respect to the following description. However, before turning to the specifics of the present systems and methods, some non-limiting examples of operational environments, such as imaging systems are provided.

Figure 3A:
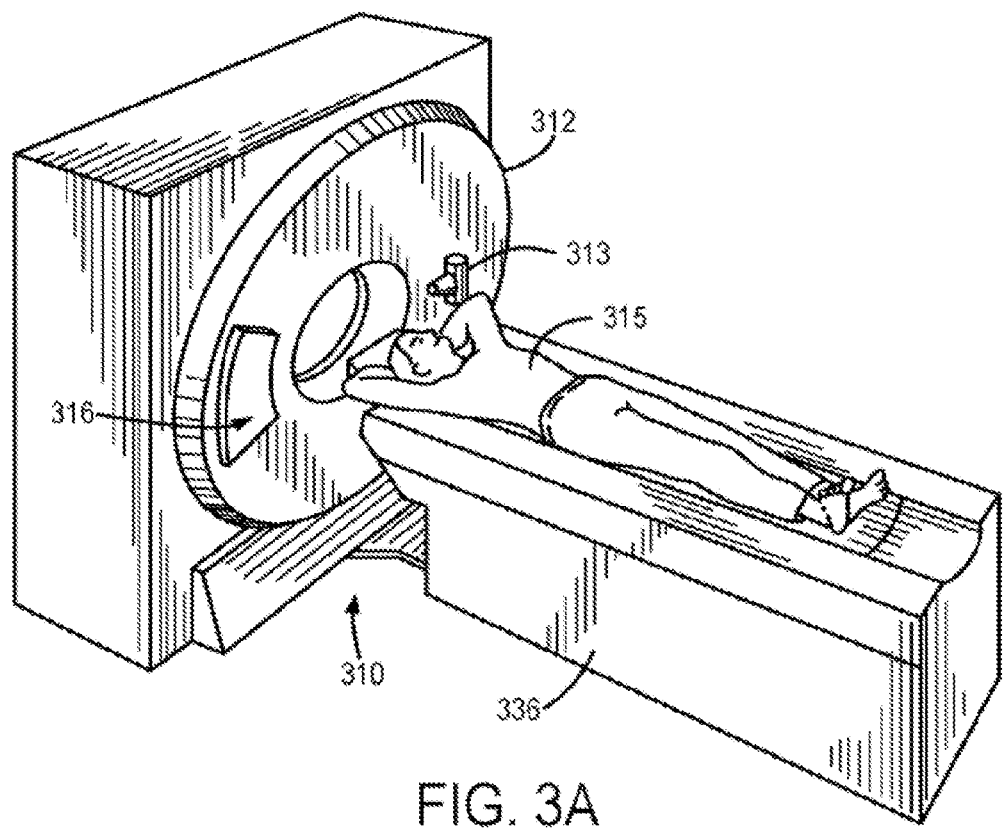
FIGS. 3A and 3B show system diagrams of an illustrative x-ray computed tomography (CT) imaging system in accordance with an embodiment.
Figure 3B:
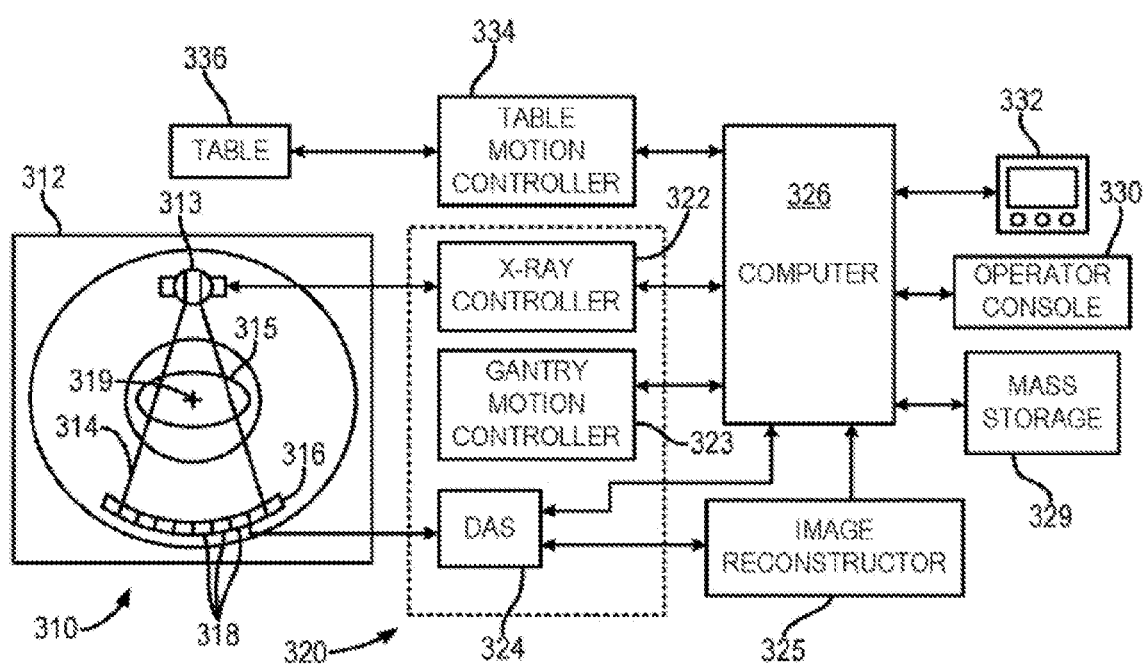

With initial reference to FIGS. 3A and 3B, an x-ray computed tomography (CT) imaging system 310 includes a gantry 312 representative of a "third generation" CT scanner. Gantry 312 has an x-ray source 313 that projects a fan beam, or cone beam, of x-rays 314 toward a detector array 316 on the opposite side of the gantry. The detector array 316 is formed by a number of detector elements 318 which together sense the projected x-rays that pass through a medical patient 315. Each detector element 318 produces an electrical signal that represents the intensity of an impinging x-ray beam and hence the attenuation of the beam as it passes through the patient. As will be described, this acquired attenuation data of a CT system 310 can be referred to as "sensor data." In the case of CT imaging, such data is typically in Radon space and measured in hounsfield units. In this way, such sensor data can be referred to as being acquired in a "sensor domain." In the case of CT imaging and its respective sensor domain, the sensor data must be transformed to an image domain, such as by using filtered backprojection, to yield a reconstructed image. However, as will be described, constraining reconstruction or acquisition based on such traditional tools for domain transfer and their inherent limitations is not necessary. Thus, as will be explained, breaking from this traditional paradigm of CT image reconstruction can yield, in accordance with the present disclosure, superior images.

During a scan to acquire x-ray projection data, the gantry 312 and the components mounted thereon rotate about a center of rotation 319 located within the patient 315. The rotation of the gantry and the operation of the x-ray source 313 are governed by a control mechanism 320 of the CT system. The control mechanism 320 includes an x-ray controller 322 that provides power and timing signals to the x-ray source 313 and a gantry motor controller 323 that controls the rotational speed and position of the gantry 312. A data acquisition system (DAS) 324 in the control mechanism 320 samples analog data from detector elements 318 and converts the data to digital signals for subsequent processing. An image reconstructor 325, receives sampled and digitized x-ray data from the DAS 324 and performs high speed image reconstruction. The reconstructed image is applied as an input to a computer 326 which stores the image in a mass storage device 328.

The computer 326 also receives commands and scanning parameters from an operator via console 330 that has a keyboard. An associated display 332 allows the operator to observe the reconstructed image and other data from the computer 326. The operator supplied commands and parameters are used by the computer 326 to provide control signals and information to the DAS 324, the x-ray controller 322 and the gantry motor controller 323. In addition, computer 326 operates a table motor controller 334 which controls a motorized table 336 to position the patient 315 in the gantry 312.

Figure 4A:
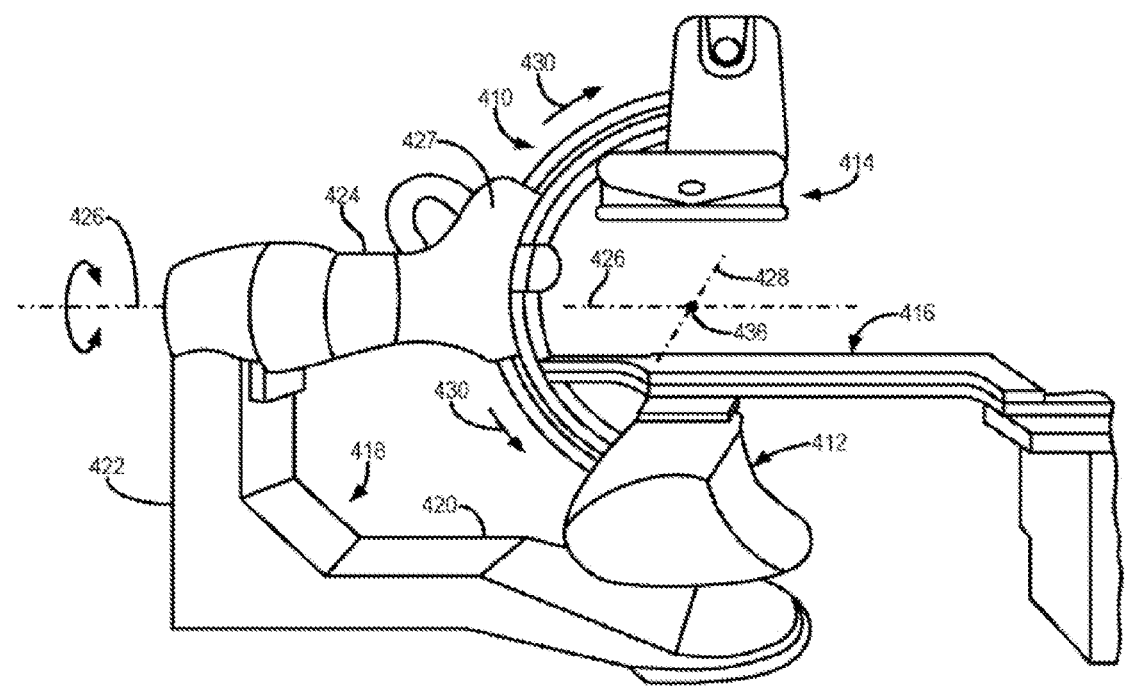
FIGS. 4A and 4B show system diagrams of another illustrative x-ray CT imaging system in accordance with an embodiment.
Figure 4B:
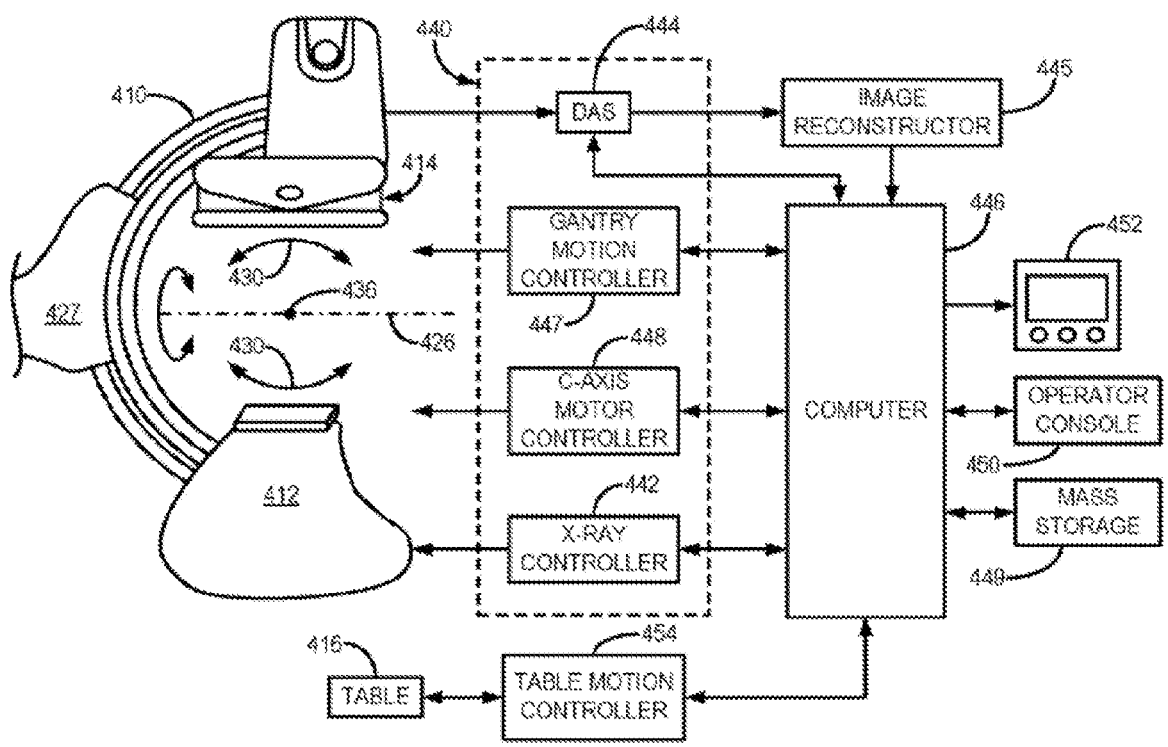

Referring particularly to FIGS. 4A and 4B, the system and method of the present disclosure may be employed to reconstruct images employs an x-ray system that is designed for use in connection with interventional procedures. It is characterized by a gantry having a C-arm 410 which carries an x-ray source assembly 412 on one of its ends and an x-ray detector array assembly 414 at its other end. Similarly to the above-described CT system 310, the data acquired by the C-arm system illustrate din FIGS. 4A and 5B can be referred to as "sensor data," in this case, typically, acquired in Radon space and measured in hounsfield units. Again, such sensor data must be transformed to an image domain, such as by using filtered backprojection, to yield a reconstructed image.

The gantry enables the x-ray source 412 and detector 414 to be oriented in different positions and angles around a patient disposed on a table 416, while enabling a physician access to the patient. The gantry includes an L-shaped pedestal 418 which has a horizontal leg 420 that extends beneath the table 416 and a vertical leg 422 that extends upward at the end of the horizontal leg 420 that is spaced from of the table 416. A support arm 424 is rotatably fastened to the upper end of vertical leg 422 for rotation about a horizontal pivot axis 426. The pivot axis 426 is aligned with the centerline of the table 416 and the arm 424 extends radially outward from the pivot axis 426 to support a C-arm drive assembly 427 on its outer end. The C-arm 410 is slidably fastened to the drive assembly 427 and is coupled to a drive motor (not shown) which slides the C-arm 410 to revolve it about a C-axis 428 as indicated by arrows 430.

The pivot axis 426 and C-axis 428 intersect each other at an isocenter 436 located above the table 416 and they are perpendicular to each other.

The x-ray source assembly 412 is mounted to one end of the C-arm 410 and the detector array assembly 414 is mounted to its other end. As will be discussed in more detail below, the x-ray source 412 emits a cone beam of x-rays which are directed at the detector array 414. Both assemblies 412 and 414 extend radially inward to the pivot axis 426 such that the center ray of this cone beam passes through the system isocenter 436. The center ray of the cone beam can thus be rotated about the system isocenter around either the pivot axis 426 or the C-axis 428, or both during the acquisition of x-ray attenuation data from a subject placed on the table 416.

Referring particularly to FIG. 4B, the rotation of the assemblies 412 and 414 and the operation of the x-ray source 432 are governed by a control mechanism 440 of the CT system. The control mechanism 440 includes an x-ray controller 442 that provides power and timing signals to the x-ray source 432. A data acquisition system (DAS) 444 in the control mechanism 440 samples data from detector elements 438 and passes the data to an image reconstructor 445. The image reconstructor 445, receives digitized x-ray data from the DAS 444 and performs high speed image reconstruction according to the methods of the present invention. The reconstructed image is applied as an input to a computer 446 which stores the image in a mass storage device 449 or processes the image further.

The control mechanism 440 also includes pivot motor controller 447 and a C-axis motor controller 448. In response to motion commands from the computer 446 the motor controllers 447 and 448 provide power to motors in the x-ray system that produce the rotations about respective pivot axis 426 and C-axis 428. A program executed by the computer 446 generates motion commands to the motor drives 447 and 448 to move the assemblies 412 and 414 in a prescribed scan path.

The computer 446 also receives commands and scanning parameters from an operator via console 450 that has a keyboard and other manually operable controls. An associated cathode ray tube display 452 allows the operator to observe the reconstructed image and other data from the computer 446. The operator supplied commands are used by the computer 446 under the direction of stored programs to provide control signals and information to the DAS 444, the x-ray controller 442 and the motor controllers 447 and 448. In addition, computer 446 operates a table motor controller 454 which controls the motorized table 416 to position the patient with respect to the system isocenter 436.

Figure 5:
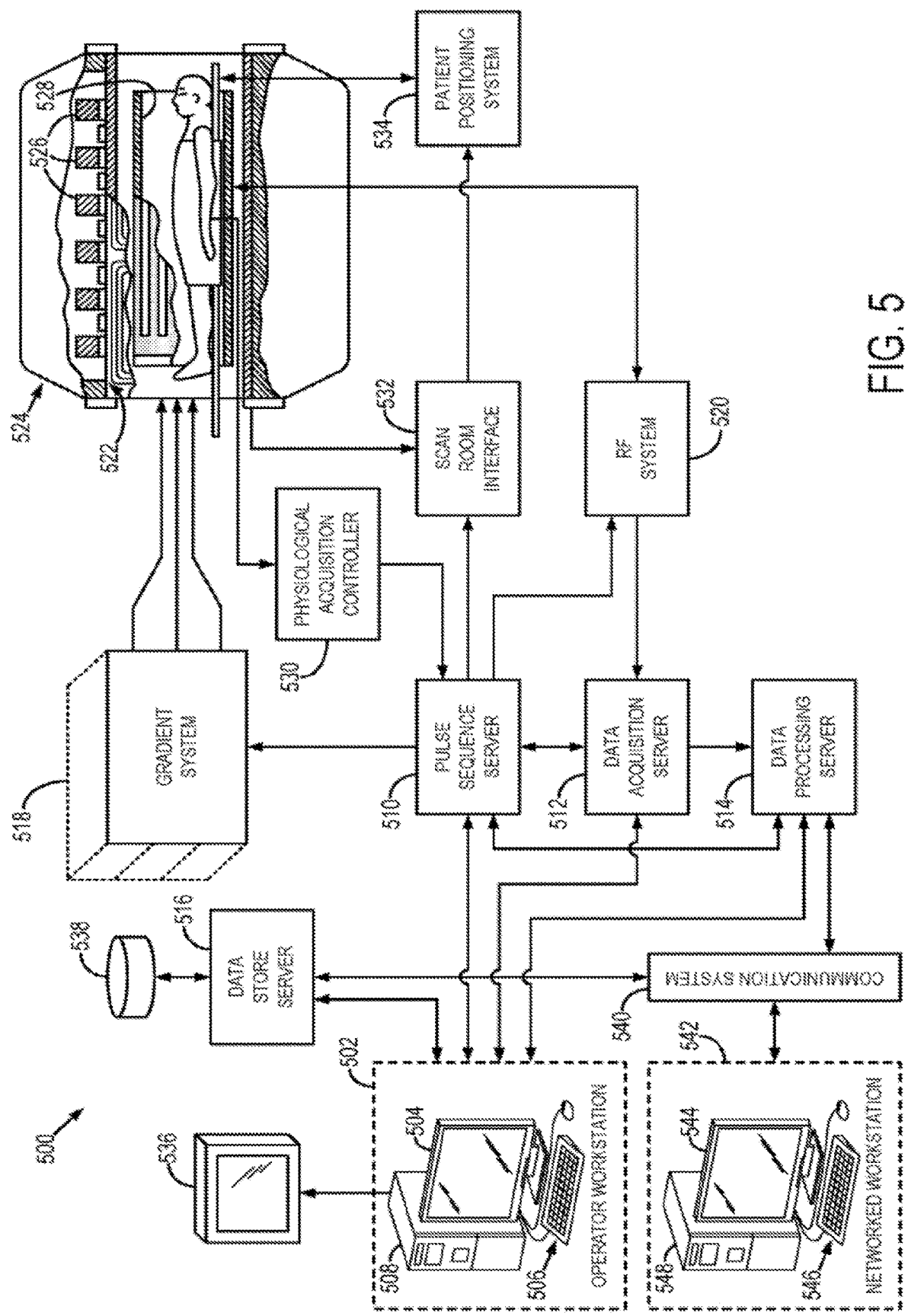
FIG. 5 shows a system diagram of an illustrative magnetic resonance imaging (MRI) system in accordance with an embodiment.

The system and methods of the present disclosure can also be applied to MR imaging systems. Referring to FIG. 5, an example of an MRI system 500 is illustrated. The MRI system 500 includes a workstation 502 having a display 504 and a keyboard 506. The workstation 502 includes a processor 508 that is commercially available to run a commercially-available operating system. The workstation 502 provides the operator interface that enables scan prescriptions to be entered into the MRI system 500. The workstation 502 is coupled to four servers: a pulse sequence server 510; a data acquisition server 512; a data processing server 514; and a data store server 516. The workstation 502 and each server 510, 512, 514, and 516 are connected to communicate with each other.

The pulse sequence server 510 functions in response to instructions downloaded from the workstation 502 to operate a gradient system 518 and a radiofrequency (RF) system 520. Gradient waveforms necessary to perform the prescribed scan are produced and applied to the gradient system 518, which excites gradient coils in an assembly 522 to produce the magnetic field gradients $G_x$, $G_y$, and $G_z$ used for position encoding MR signals. The gradient coil assembly 522 forms part of a magnet assembly 524 that includes a polarizing magnet 126 and a whole-body RF coil 528 and/or local coil.

RF excitation waveforms are applied to the RF coil 528, or a separate local coil, such as a head coil, by the RF system 520 to perform the prescribed magnetic resonance pulse sequence. Responsive MR signals detected by the RF coil 528, or a separate local coil, are received by the RF system 520, amplified, demodulated, filtered, and digitized under direction of commands produced by the pulse sequence server 510. The RF system 520 includes an RF transmitter for producing a wide variety of RF pulses used in MR pulse sequences. The RF transmitter is responsive to the scan prescription and direction from the pulse sequence server 510 to produce RF pulses of the desired frequency, phase, and pulse amplitude waveform. The generated RF pulses may be applied to the whole body RF coil 528 or to one or more local coils or coil arrays.

The RF system 520 also includes one or more RF receiver channels. Each RF receiver channel includes an RF preamplifier that amplifies the MR signal received by the coil 528 to which it is connected, and a detector that detects and digitizes the quadrature components of the received MR signal. The magnitude of the received MR signal may thus be determined at any sampled point by the square root of the sum of the squares of the I and Q components:

$$M = \sqrt{I^2 + Q^2} \qquad (1),$$

and the phase of the received MR signal may also be determined:

$$\varphi = \tan^{-1}\left(\frac{Q}{I}\right). \qquad (2)$$

In the case of an MRI system 500, these acquired RF signals are sampled in "k-space," which is a frequency domain. Thus, the MRI system 500 acquires "sensor data" in the frequency domain, which represents the "sensor domain" for MR or NMR imaging. Such MR sensor data must be transformed to an image domain to yield a reconstructed image, which is traditionally achieved via a Fourier transform or projection reconstruction technique. However, as will be described, constraining reconstruction or acquisition based on such traditional tools for domain transfer and their inherent limitations is not necessary. Thus, as will be explained, breaking from this traditional paradigm of MR image reconstruction can yield, in accordance with the present disclosure, superior images.

The pulse sequence server 510 also optionally receives patient data from a physiological acquisition controller 530. The controller 530 receives signals from a number of different sensors connected to the subject to be scanned, such as electrocardiograph (ECG) signals from electrodes, or respiratory signals from a bellows or other respiratory monitoring device. Such signals are typically used by the pulse sequence server 510 to synchronize, or "gate," the performance of the scan with the subject's heart beat or respiration.

The pulse sequence server 510 also connects to a scan room interface circuit 532 that receives signals from various sensors associated with the condition of the patient and the magnet system. A patient positioning system 532 may be included.

The digitized MR signal samples produced by the RF system 520 are received by the data acquisition server 512. The data acquisition server 512 operates in response to instructions downloaded from the workstation 502 to receive the real-time MR data and provide buffer storage, such that no data is lost by data overrun. In some scans, the data acquisition server 512 does little more than pass the acquired MR data to the data processor server 514. However, in scans that require information derived from acquired MR data to control the further performance of the scan, the data acquisition server 512 is programmed to produce such information and convey it to the pulse sequence server 510. For example, during prescans, MR data is acquired and used to calibrate the pulse sequence performed by the pulse sequence server 510. Also, navigator signals may be acquired during a scan and used to adjust the operating parameters of the RF system 520 or the gradient system 518, or to control the view order in which k-space data (e.g., frequency domain data) is sampled. In all these examples, the data acquisition server 512 acquires MR data and processes it in real-time to produce information that is used to control the scan.

The data processing server 514 receives MR data from the data acquisition server 512 and processes it in accordance with instructions downloaded from the workstation 502. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 514 are conveyed back to the workstation 502 where they are stored. Real-time images are stored in a data base memory cache (not shown), from which they may be output to operator display 504 or a display 536 that is located near the magnet assembly 524 for use by attending physicians. Batch mode images or selected real time images are stored in a host database on disc storage 538. When such images have been reconstructed and transferred to storage, the data processing server 514 notifies the data store server 516 on the workstation 502. The workstation 502 may be used by an operator to archive the images, produce films, or send the images via a network or communication system 540 to other facilities that may include other networked workstations 542.

The communication system 540 and networked workstation 542 may represent any of the variety of local and remote computer systems that may be included within a given imaging facility including the system 500 or other, remote location that can communicate with the system 500. In this regard, the networked workstation 542 may be functionally and capably similar or equivalent to the operator workstation 502, despite being located remotely and communicating over the communication system 540. As such, the networked workstation 542 may have a display 544 and a keyboard 546. The networked workstation 542 includes a processor 548 that is commercially available to run a commercially-available operating system. The networked workstation 542 may be able to provide the operator interface that enables scan prescriptions to be entered into the MRI system 500.

Figure 6:
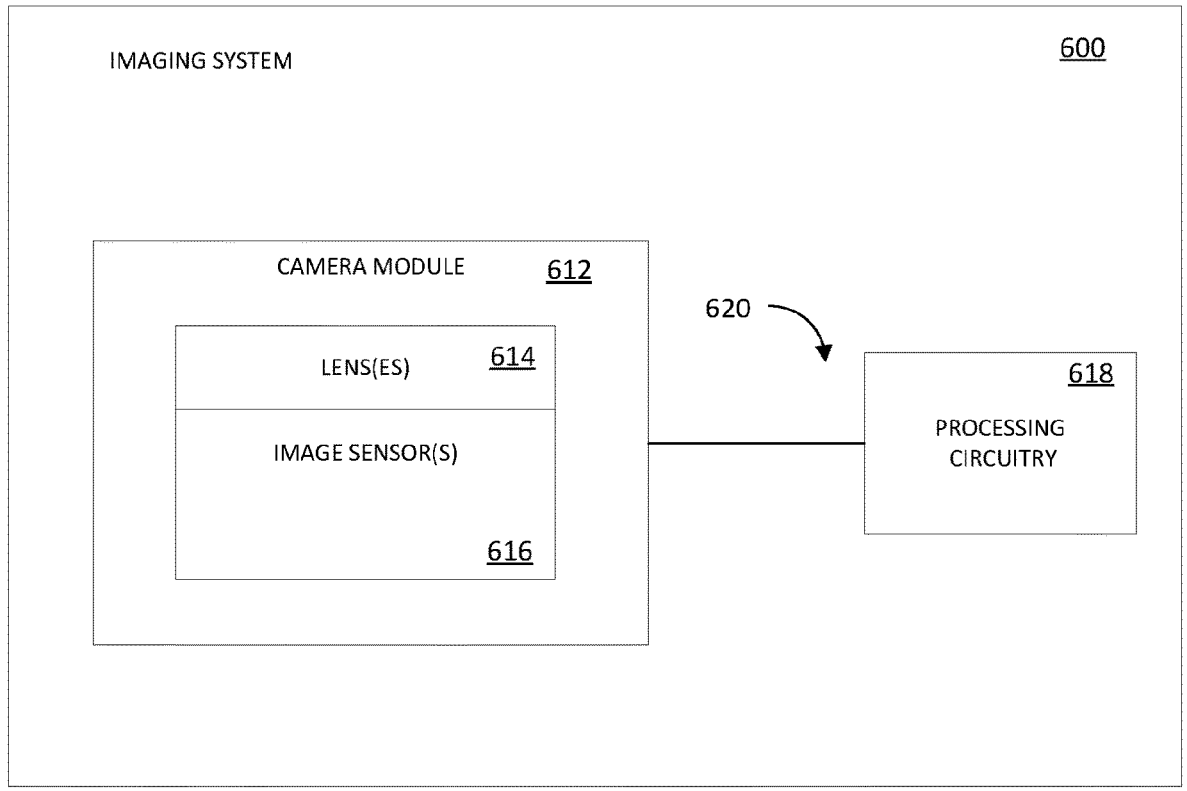
FIG. 6 shows a system diagram of an illustrative electronic device that uses one or more image sensors to optically capture images in accordance with an embodiment.

FIG. 6 is a diagram of an illustrative electronic device that uses one or more image sensors to capture images and that includes processing circuitry configured to execute an AUTOMAP image reconstruction algorithm of the type described in connection with FIGS. 8-11. An imaging system 610 may be a portable imaging system such as a camera, a cellular telephone, a video camera, or any other imaging device that captures digital image data. A camera module 612 may be used to convert incoming light into digital image data. The camera module 612 includes one or more lenses 614 and one or more corresponding image sensors 616. In some embodiments, the lens 614 may be part of an array of lenses and image sensor 616 may be part of an image sensor array.

Processing circuitry 618 may include one or more integrated circuits (e.g., image processing circuits, microprocessors, storage devices such as random-access memory and non-volatile memory, etc.) and may be connected via in input 620 to the camera module 612 and/or that form part of the camera module 612 (e.g., circuits that form part of an integrated circuit that includes the image sensor 616 or an integrated circuit within the camera module 612 that is associated with the image sensor 616). Image data that has been captured and processed by the camera module 612 may, if desired, be further processed and stored using the processing circuitry 618. Processed image data may, if desired, be provided to external equipment, such as a computer or other electronic device, using wired and/or wireless communication paths coupled to the processing circuitry 618. For example, the processing circuitry 618 may include a field programmable gate array (FPGA) or an application specific integrated circuit (ASIC), with which the AUTOMAP data-driven manifold learning processes may be performed (e.g., using neural networks such as the networks in the system 900 of FIG. 9) in order to execute generalized image reconstruction techniques to transform raw data (e.g., pixel voltages) generated by the image sensor 616 into images in the image domain (e.g., a spatial domain in which the arrangement and relationship among different pixel values are expressed) without the use of human-devised acquisition-specific mathematical functions.

For example, an array of photo-sensitive pixels within the image sensor 616 may generate an array of pixel voltages corresponding to a captured image when exposed to light. This array of pixel voltages may be transformed into visual representations of the captured image in the image domain using a learned (e.g., trained) AUTOMAP image reconstruction process (e.g., using a neural network such as the networks in the system 900 of FIG. 9) executed by the processing circuitry 618. For example, a neural network may be used to transform digital voltages output by analog-to-digital converter (ADC) circuitry (e.g., that processes the outputs of the pixels of the image sensor 616) to the image domain.

Digital photography and cinematography performed in low-light conditions may result in low-quality images and videos due to image sensor non-idealities (e.g., thermal noise of CCD and CMOS image sensors or read-out noise of on-chip amplifiers in the image sensor) when using traditional image processing techniques. By using learned AUTOMAP image reconstruction (neural networks) in place of traditional image processing techniques, image sensor defects may be automatically compensated for and, because learned image reconstruction may be robust to corruptive channel noise such as additive white Gaussian noise, signal-to-noise ratio (SNR) for the image may be comparatively improved, especially when the learned image reconstruction is trained using real-world representative data (images).

Figure 7:
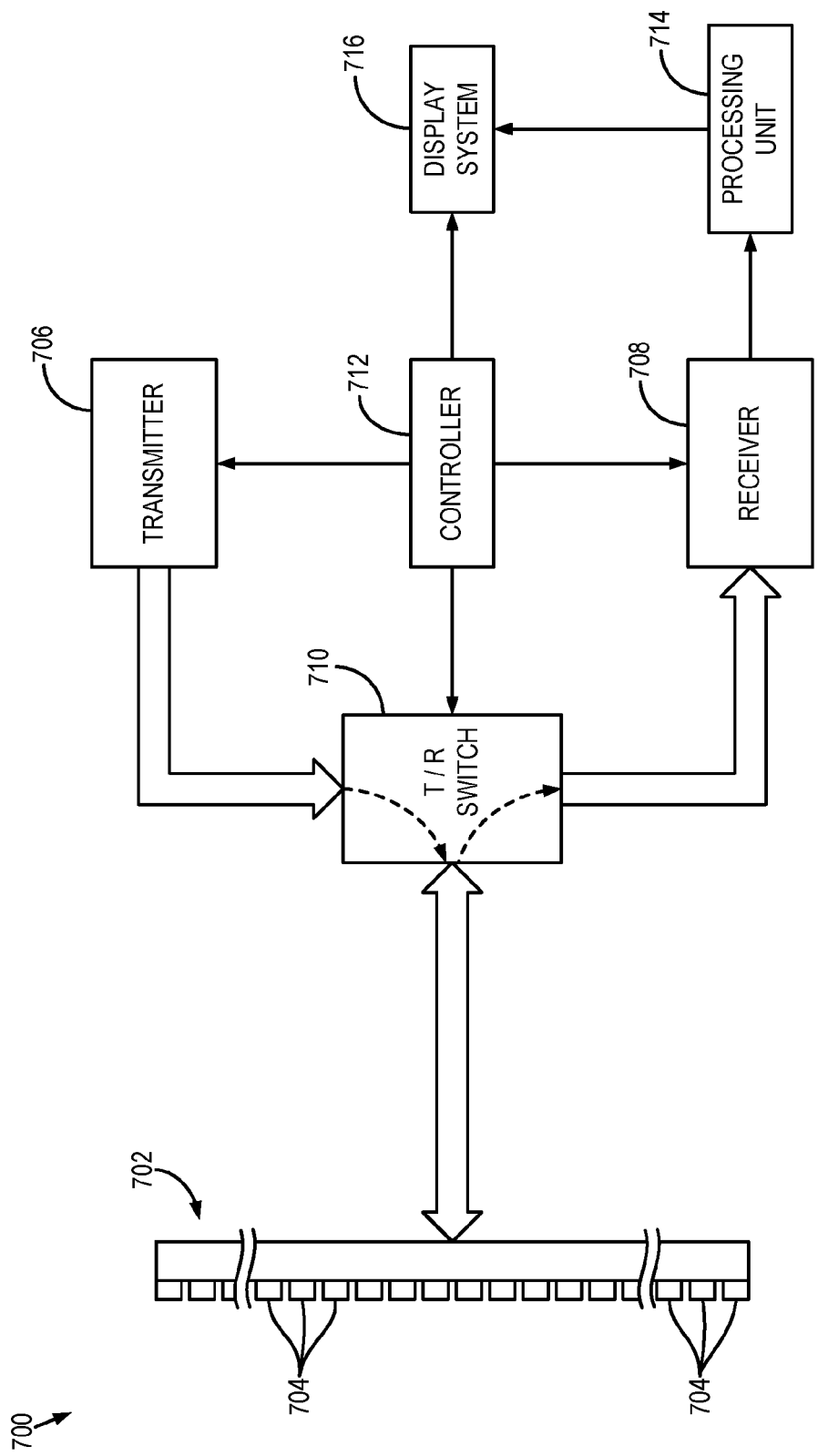
FIG. 7 shows a system diagram of an illustrative ultrasound system in accordance with an embodiment.

FIG. 7 illustrates an example of an ultrasound system 700 that can implement the methods described in the present disclosure. The ultrasound system 700 includes a transducer array 702 that includes a plurality of separately driven transducer elements 704. The transducer array 702 can include any suitable ultrasound transducer array, including linear arrays, curved arrays, phased arrays, and so on. Similarly, the transducer array 702 can include a 1D transducer, a 1.5D transducer, a 1.75D transducer, a 2D transducer, a 3D transducer, and so on.

When energized by a transmitter 706, a given transducer element 704 produces a burst of ultrasonic energy. The ultrasonic energy reflected back to the transducer array 702 (e.g., an echo) from the object or subject under study is converted to an electrical signal (e.g., an echo signal) by each transducer element 704 and can be applied separately to a receiver 708 through a set of switches 710. The transmitter 706, receiver 708, and switches 710 are operated under the control of a controller 712, which may include one or more processors. As one example, the controller 712 can include a computer system.

The transmitter 706 can be programmed to transmit unfocused or focused ultrasound waves. In some configurations, the transmitter 706 can also be programmed to transmit diverged waves, spherical waves, cylindrical waves, plane waves, or combinations thereof. Furthermore, the transmitter 706 can be programmed to transmit spatially or temporally encoded pulses.

The receiver 708 can be programmed to implement a suitable detection sequence for the imaging task at hand. In some embodiments, the detection sequence can include one or more of line-by-line scanning, compounding plane wave imaging, synthetic aperture imaging, and compounding diverging beam imaging.

In some configurations, the transmitter 706 and the receiver 708 can be programmed to implement a high frame rate. For instance, a frame rate associated with an acquisition pulse repetition frequency ("PRF") of at least 100 Hz can be implemented. In some configurations, the ultrasound system 700 can sample and store at least one hundred ensembles of echo signals in the temporal direction.

The controller 712 can be programmed to design an imaging sequence. In some embodiments, the controller 712 receives user inputs defining various factors used in the design of the imaging sequence.

A scan can be performed by setting the switches 710 to their transmit position, thereby directing the transmitter 706 to be turned on momentarily to energize transducer elements 704 during a single transmission event according to the designed imaging sequence. The switches 710 can then be set to their receive position and the subsequent echo signals produced by the transducer elements 704 in response to one or more detected echoes are measured and applied to the receiver 708. The separate echo signals from the transducer elements 704 can be combined in the receiver 708 to produce a single echo signal.

The echo signals are communicated to a processing unit 714, which may be implemented by a hardware processor and memory, to process echo signals or images generated from echo signals. As an example, the processing unit 714 can implement AUTOMAP image reconstruction, including realizing a neural network (e.g., the networks in the system 900 of FIG. 9) for transforming the echo signals (e.g., raw data in the sensor domain in which the ultrasound system 700 operates) into a visual representation (e.g., an image in the image domain) of the object or subject under study, or of a portion thereof, using the methods described in the present disclosure. Images produced from the echo signals by the processing unit 714 can be displayed on a display system 716.

Figure 8:
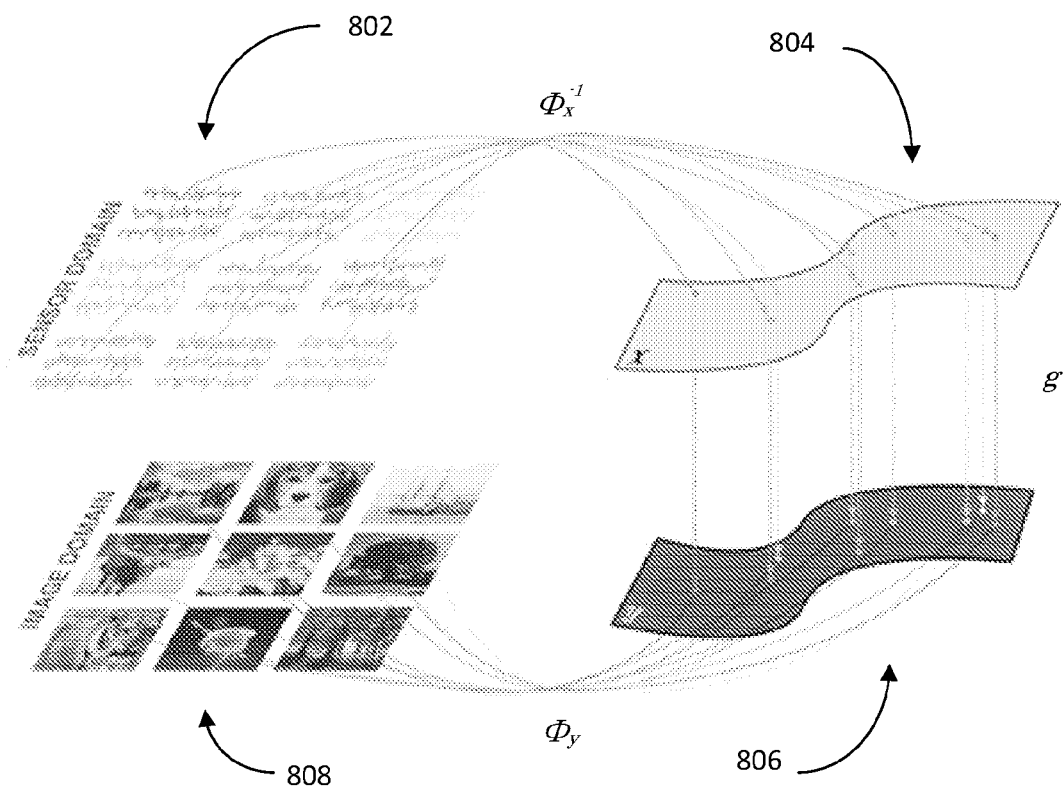
FIG. 8 shows an illustrative process flow diagram representing a process for generic image reconstruction between a sensor domain and an image domain using data-driven manifold learning in accordance with an embodiment.

FIG. 8 shows an illustrative flow diagram representing a process for general image reconstruction between a sensor domain and an image domain using data-driven manifold learning (e.g., using neural networks). Sensor data 802 may be generated when an image is captured using any one of a variety of imaging systems including, but not limited to, a magnetic resonance imaging (MRI) system, a computed tomography (CT) scanning system, a positron emission tomography (PET) scanning system, an ultrasound system, an optical complementary metal oxide semiconductor (CMOS) imaging system, and an optical charge coupled device (CCD) image sensor. Sensor data 802 may be acquired or encoded in a particular domain corresponding to the particular method of image capture used to acquire/generate the sensor data 802, which can be referred to herein as the "sensor domain." Any noise that may be present within the sensor data 802 (e.g., as a result of non-idealities involved with image capture) is inherently intertwined with the sensor data. As described above, the sensor data 802 may be encoded in one of a variety of different domains (e.g., frequency domain, Radon domain, etc.) depending on the method of data acquisition used, the domain of any given set of sensor data may be referred to herein generally as the sensor domain. By transforming the sensor data 802 from the sensor domain to the image domain to produce image data 808, the sensor data 802 may be effectively decoded.

In FIG. 8, $\chi$ represents the sensor data 802 in the sensor domain, and y represents image data 808 in the image domain. Given $\tilde{\chi}$ the noisy observation of sensor domain data $\chi$, the stochastic projection operator onto $\chi$: $p(\tilde{\chi})=P(\chi|\tilde{\chi})$ may be learned. After obtaining $\chi$, the second task is to reconstruct $f(\chi)$ by producing a reconstruction mapping $f: \mathbb{R}^{n^2} \to \mathcal{M}_{xy}$ that minimizes the reconstruction error $L(\hat{f}(\chi), f(\chi))$.

With this starting context, the reconstruction process can be described for an idealized scenario, for example, where the input sensor data are noiseless. Denote the data as $(y_i, \chi_i)_{i=1}^n$, where for $i^{th}$ observation $\chi_i$ indicates a n×n set of input parameters, and $y_i$ indicates the n×n real, underlying images. It may be assumed that (1) there exists a unknown smooth and homeomorphic function $f: \mathbb{R}^{n^2} \to \mathbb{R}^{n^2}$, such that $y=f(\chi)$, and (2) $(\chi_i)_{i=1}^n$, $(y_i)_{i=1}^n$, lie on unknown smooth manifolds $\chi$ and $\mathcal{Y}$ (e.g., manifolds 804 and 806), respectively.

Both manifolds 804 and 806 are embedded in the ambient space $\mathbb{R}^{n^2}$, such that $\dim(\chi) < n^2$ and $\dim(\mathcal{Y}) < n^2$.

The above two assumptions combine to define a joint manifold $\mathcal{M}_{xy} = \mathcal{X} \times \mathcal{Y}$ that the dataset $(\chi_i, y_i)_{i=1}^n$ lies in, which can be written as:

$$\mathcal{M}_{xy} = \{(\chi, f(\chi)) \in \mathbb{R}^{n^2} \times \mathbb{R}^{n^2} | \chi \in \mathcal{X}, f(\chi) \in \mathcal{Y}\}.$$

Note, $(\chi, f(\chi))$ is described using the regular Euclidean coordinate system. However, we may equivalently describe this point using the intrinsic coordinate system of $\mathcal{M}_{xy}$ as $(z, g(z))$ such that there exists a homeomorphic mapping $\phi = (\phi_x, \phi_y)$ between $(\chi, f(\chi))$ and $(z, g(z))$ (i.e. $x = \phi_x(z)$ and $f(\chi) = \phi_y \circ g(z)$ As a side note, in topology, $\phi = (\phi_x, \phi_y): \mathcal{M}_{xy} \to \mathbb{R}^{n^2} \times \mathbb{R}^{n^2}$ may correspond to the local coordinate chart of $\mathcal{M}_{xy}$ at the neighborhood of $(\chi, f(\chi))$. Instead of directly learning $f$ in the ambient space, it may be desirable to learn the diffeomorphism $g$ between $\mathcal{X}$ and $\mathcal{Y}$ in order to take advantage of the low-dimensional nature of embedded space. Consequently, the process of generating $y=f(\chi)$ from $\chi$ can be written as a sequence of function evaluations:

$$f(\chi) = \phi_y \circ g \circ \phi_x^{-1}(\chi).$$

For the convenience of later presentation, we notice that given input image $\chi$, the output image follows a probability distribution $Q(Y|X=\chi, f)$, which is a degenerate distribution with point mass at $y=f(\chi)$.

With the context provided by this idealized sensor data that is free of noise in place, a non-ideal scenario, where noise or other corruption exists in the sensor domain input and a corresponding de-noising process, are now described. Instead of observing the perfect input data $\chi_i$, $\tilde{\chi}_i$ is observed, which is sensor data with noise or a corrupted version of $\chi_i$ by some known noise or corruption process described by the probability distribution $P(\tilde{X}|X=\chi)$. In order to handle this complication, a denoising step $Q(X|\tilde{X}=\tilde{\chi}, p)$ may be used to our model pipeline, such that our prediction for y is no longer a deterministic value, but a random variable with conditional distribution $P(Y|\tilde{X})$ so that the prediction uncertainty caused by the corruption process may be properly characterized.

Instead of learning this denoising step explicitly, an analogy may be drawn from denoising autoencoders. The joint distribution $P(Y, X, \tilde{X})$ may be modeled instead. Specifically, in addition to the assumptions (1)-(2) listed above, we also assume (3) the true distribution $P(Y|\tilde{X})$ lies in the semiparametric family $\mathbb{Q}$ defined by its first moment $\mathbb{Q} = \{Q(X|\tilde{X}=\tilde{\chi}, p) | E(X) = p(\tilde{X})\}$.

$P(Y, X, \tilde{X})$ may be modeled using the decomposition below:

$$Q_{(f,p)}(Y, X, \tilde{X}) = Q(Y|X, f)Q(X|\tilde{X}, p)P(\tilde{X}).$$

where $Q(Y|X, f)$ denote the model for reconstruction process described above, $Q(X|\tilde{X}, p)$ denote the de-noising operator, and $P(\tilde{X})$ denotes the empirical distribution of corrupted images. Notice that the models for de-noising and reconstruction processes may be combined together by collapsing the first two terms on the right-hand side into one term, which gives:

$$Q_{(f,p)}(Y, X, \tilde{X}) = Q(Y, X|\tilde{X}, (f, p))P(\tilde{X}).$$

It should be noted that Y=f(X) is a deterministic and homeomorphic mapping of X; therefore, $Q(Y, X|\tilde{X}, (f, p)) = Q(Y|\tilde{X}, (f, p))$ is the predictive distribution of output image y given the noisy input $\tilde{\chi}$, which is the estimator of interest. Consequently, the model can be written as:

$$Q_{(f,p)}(Y, X, \tilde{X}) = Q(Y|\tilde{X}, (f, p))P(\tilde{X}).$$

This then represents a definition of the model for the joint distribution.

In the actual training stage, "perfect" (e.g., substantially noiseless) input images $\chi$ are available, and the model can be trained with $\tilde{\chi}$ that is generated from $P(\tilde{X}|X=x)$. That is to say, the joint distribution of $(Y, X, \tilde{X})$ observed in training data admits the form:

$$P(Y, X, \tilde{X}) = P(Y|X)P(\tilde{X}|X)P(X).$$

The training can proceed by minimizing the KL-divergence between observed probability $P(Y, X, \tilde{X})$ and the model $Q(Y, X, \tilde{X})$, $$\mathbb{D}_{KL}\{P(Y, X, \tilde{X}) \| Q_{(f,p)}(Y, X, \tilde{X})\},$$

with respect to the function-valued parameters (f,p). As the KL-divergence converges toward 0, $Q(X|\tilde{X}, p)$ converges to P(X|X̃) the de-noising projection, and at the same time Q(Y|X̃,((f,p)) converges to P(X|X).

It should be noted that techniques for the explicit learning of the stochastic projection p, diffeomorphism g, and the local coordinate chart φ exist. However, we notice that, since $(\phi_f, \phi_x, p, g) \in \mathbb{C}^\infty$ (where $\mathbb{C}^\infty$ denotes the set of infinitely differentiable functions), $\hat{f} = \phi_f \circ g \circ \phi_x^{-1} \circ p$ as a whole is a continuously differentiable function on a compact subset of $\mathbb{R}^{n^2}$, and can therefore be approximated with theoretical guarantee by the universal approximation theorem.

Figure 9:
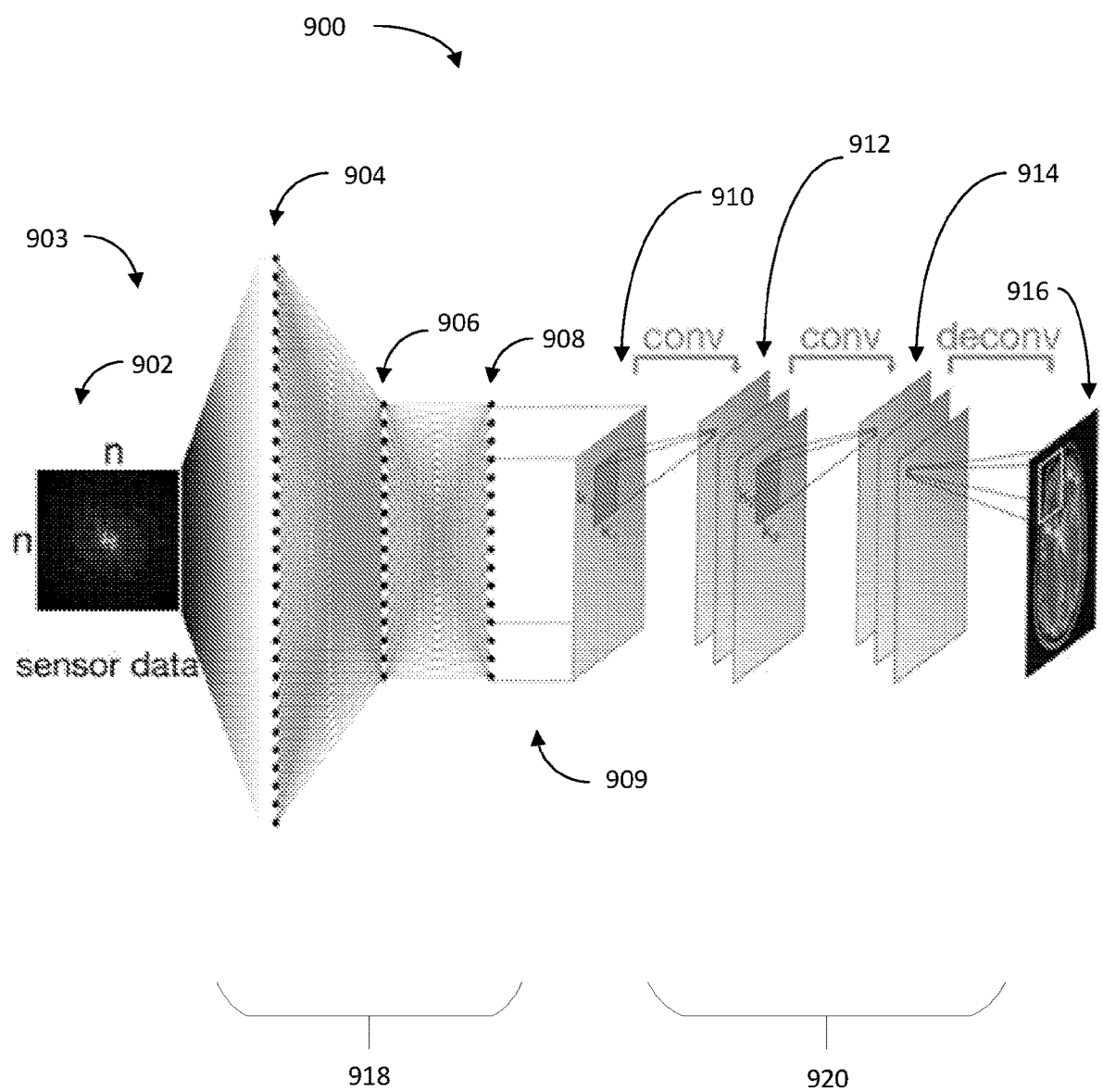
FIG. 9 shows an illustrative system diagram representing a neural network configured to reconstruct an image by transforming data from a sensor domain to an image domain in accordance with an embodiment.

FIG. 9 shows an illustrative diagram representing a system 900 that implements AUTOMAP image processing and, thereby, is configured to transform sensor data (e.g., sensor data 802 of FIG. 8) from the sensor domain into the image domain, thereby reconstructing the sensor data 902 into an image. The system 900 may be an example of data-driven manifold learning as described above in connection with FIG. 8.

The sensor data 902 may be arranged in an "n×n" matrix in the sensor domain 903. Fully connected layers 918 may include input layer 904, hidden layer 906, and hidden layer 908. Each fully connected layer of the fully connected layers 918 of the neural network may include nodes. Each of these nodes may be fully connected to the nodes of an adjacent fully connected layer according to weights assigned to the edges of the nodes. These nodes may store values produced during the application of the layer in which the nodes are included (e.g., the application of the layer to another matrix or vector), and may be considered to be the output (e.g., a matrix output) of that layer. The fully connected layers 918 may be applied to the sensor data 902 in order to approximate the between-manifold projection of sensor data 902 from the sensor domain 903 to the image domain 909. In this way, the fully connected layers 918 produce "n×n" matrix 910. The convolutional layers 920 are then applied to the matrix 910. The convolutional layers 920 may include a first convolutional layer 912 and second convolutional layer 914, and may produce a reconstructed image at an output layer 916. Here, "n" represents the number of data points along a single dimension of the sensor data 902.

The sensor data 902 may include a vector or matrix of sensor domain sampled data produced, for example, by an imaging system (e.g., one of the imaging systems of FIGS. 1-7). The input layer 904 may be fully connected to the first hidden layer 906, which may allow the sensor data 902 to be vectorized in any order. Complex data in the sensor data 902 (e.g., such as MR data) may be separated into real and imaginary components and concatenated in an input vector at input layer 904. As a result, the "n×n" matrix of the sensor data 902 may be reshaped to a "$2n^2 \times 1$" real-valued vector (e.g., the input vector) containing both the real and imaginary components of the sensor data 902. The input layer 904 may be fully connected to an "$n^2 \times 1$" first hidden layer 906 that is activated by an activation function (e.g., a non-linear activation function such as the hyperbolic tangent function). The first hidden layer 906 may be fully connected to a second "$n^2 \times 1$" hidden layer 908, which may produce a "n×n" matrix 910 when applied to the output fo the hidden layer 906. Each of the fully connected layers 918 may represent affine mapping (e.g, matrix multiplication) followed by a non-linearity (e.g., an activation function). For example, the non-linearity applied during the application of the first hidden layer 906 to the input vector (e.g., to the nodes of the input vector) may be represented by the following equation:

$$g(\chi) = s(W\chi + b)$$

where g(x) is a matrix (e.g., the nodes/output of the first hidden layer) resulting from the application of the first hidden layer 906 to the input vector, where is the input vector (e.g., the nodes/output of the input layer), where W is a d'×d weight matrix, where b is an offset vector of dimensionality d', and where s is the activation function (e.g., the hyperbolic activation function). The non-linearity applied during the application of the second hidden layer 908 to the output of the first hidden layer (e.g. to the nodes of the first hidden layer) may be similarly represented.

The convolutional layer 912 may apply a predetermined number of filters to the matrix 910 followed by a rectifier nonlinearity. The second convolutional layer 914 may apply a predetermined number of filters to the outputs of the first convolutional layer 912 followed by a rectifier nonlinearity. The output of the second convolutional layer 914 may be de-convolved with a predetermined number of filters by applying the output layer 916 to produce a reconstructed image in the image domain (e.g., as an "n×n" matrix). In this way, the first and second convolutional layers 912, 914 may be applied to perform feature extraction after the sensor data 902 is transformed from the sensor domain 903 into the image domain 909.

It should be understood that the system 900 is trained to perform image reconstruction before being implemented. For example, an image may be transformed from the image domain 909 to a given sensor domain 903 (e.g., frequency domain, Radon domain, etc.) using known operations to produce sensor data 902. This sensor data 902 may then be input into and processed by system 900 to perform training. The output of system 900 may then be analyzed and compared to the original image to determine the amount of error present in the reconstructed image. The weights of the networks with in the system 900 (e.g., the weights between layers 904 and 906 and between layers 906 and 908) may then be adjusted and this training process is repeated with a new image. For example, the training process may be repeated a predetermined number of times or may be repeated until the amount of observed error in the reconstructed image is observed to be below a certain threshold.

It should be noted that for instances in which the system 900 is intended to be used for a particular image reconstruction purpose (e.g., reconstructing images of the human brain), it may be beneficial to train neural networks in the system 900 using images related to that purpose (e.g., using images of the human brain). This image-based training specialization may result in improved hidden-layer activation sparsity for fully connected layers 918 of the system 900 without the need to impose a sparsifying penalty on these layers. Improving hidden layer activation sparsity in this way may provide benefits over comparatively dense hidden layer activations. For example, these benefits may include reduced information entangling, more efficient variable-size representation, improved likelihood of linear separability, and improved efficiency, compared to dense hidden layer activations.

Figure 10:
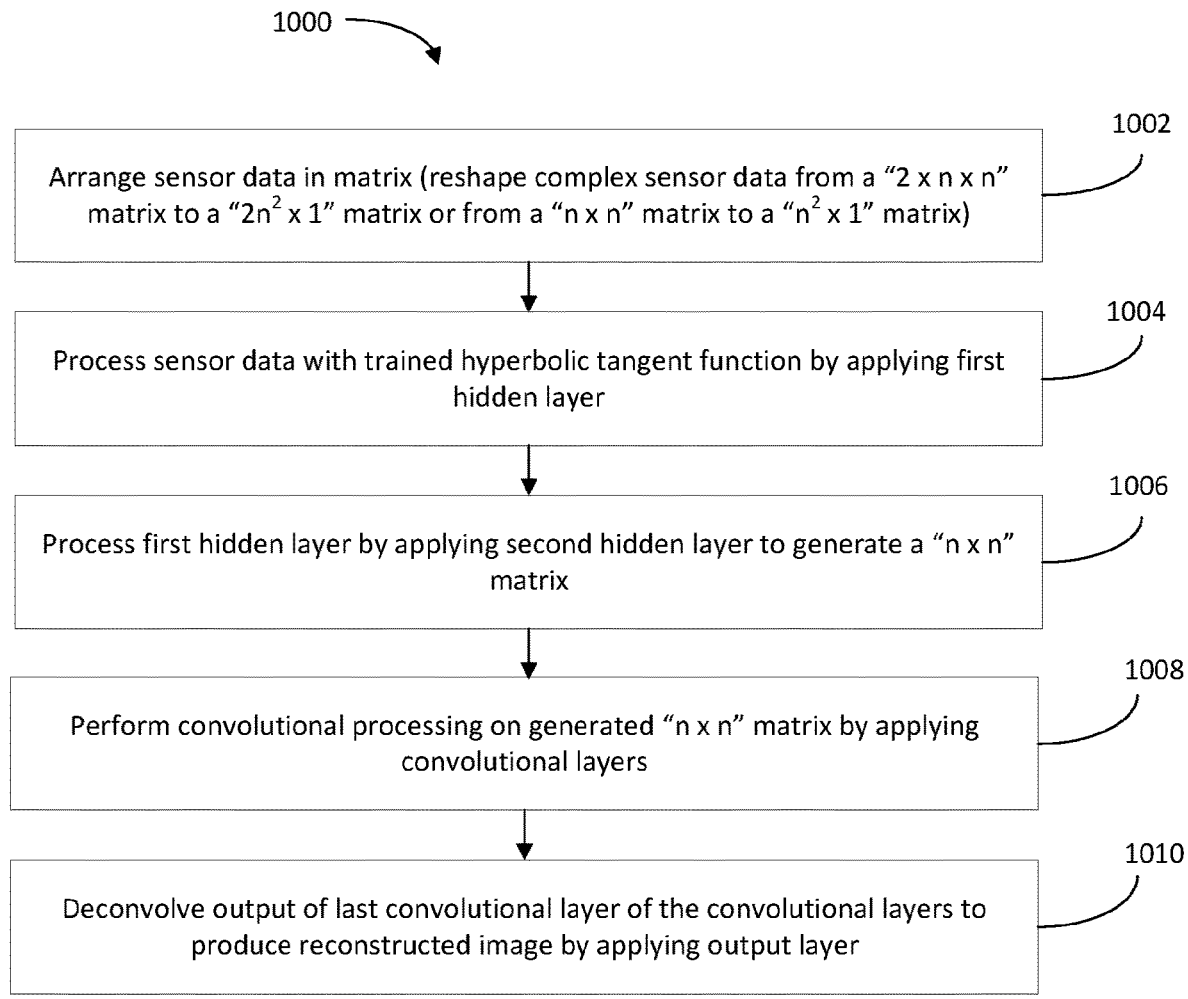
FIG. 10 shows an illustrative process flow diagram that may be performed by the neural network of FIG. 9 in order to reconstruct an image in accordance with an embodiment.

FIG. 10 shows an illustrative process 1000 that may be performed to realize an AUTOMAP technique, such as using a neural network (e.g., the networks in the system 900 of FIG. 9) executed by processing circuitry (e.g., in the data processing server 514 of FIG. 5, the processing circuitry 618 of FIG. 6, or the controller 712 of FIG. 7) to reconstruct an image from raw sensor data (e.g., the sensor data 902 of FIG. 9).

At 1002, the sensor data is arranged in a matrix at an input layer (e.g., the layer 904 of FIG. 9). As described, in some instances it may be advantageous to reshape the sensor data from a "2×n×n" matrix to a "2n²×1" matrix, such as when the sensor data is complex data, as is the case in MR imaging. If in such instances, the sensor data may be reshaped by concatenating real components of the sensor data with imaginary components of the sensor data at an input layer of the neural network for instances in which the sensor data is complex (e.g., as may be the case with k-space data). This separation and subsequent concatenation of real and imaginary data may be beneficial for instances in which the computational framework of the neural network operates using only real-valued inputs and parameters. Otherwise, for instances in which the sensor data is not complex, the sensor data may be reshaped from a "n×n" matrix to a "n²×1" matrix at the input layer.

At 1004, the matrix of sensor data is processed with a trained activation function at a first hidden layer (e.g., hidden layer 906 of FIG. 9) of the neural network having dimensions "n²×1". This activation function, for example, may be a non-linear activation function. The first hidden layer may be a fully connected layer, meaning that each neuron of the first hidden layer is respectively connected to each neuron of the input layer. The trained activation function may include any of, for example, hyperbolic tangent, sigmoidal, or rectified linear units activation functions or other activation functions.

At 1006, a second hidden layer of the neural network having dimensions "n²×1" is applied to the output of the first hidden layer (e.g., to the matrix produced when the first hidden layer is applied to the input vector). The second hidden layer may be a fully connected layer, meaning that each neuron of the second hidden layer is respectively connected to each neuron of the first hidden layer. The second hidden layer may re-shape the first hidden layer into an "n×n" matrix.

At 1008, convolutional processing is performed on the generated "n×n" matrix using convolutional layers (e.g., convolutional layers 920 of FIG. 9). A first convolutional layer (e.g., convolutional layer 912 of FIG. 9) may be applied to the generated "n×n" matrix in order to apply a predetermined number of filters (e.g., convolutional filters), each having predetermined dimensions and a predetermined stride, to the "n×n" matrix. A second convolutional layer (e.g., convolutional layer 914 of FIG. 9) may be applied to the output of the first convolutional layer in order to apply a predetermined number of filters (e.g., convolutional filters), each having predetermined dimensions and a predetermined stride, to the output of the first convolutional layer. Such convolutional processing may, for example, be particularly advantageous in achieving an additional level of feature extraction. For example, an initial layer of feature extraction may be achieved by the image reconstruction performed by the domain transfer into the image domain from the sensor domain and/or the feature extraction may be achieved by the conversional layers.

At 1010, the output of the second convolutional layer (e.g., the last convolutional layer of the convolutional layers) is deconvolved to produce a final reconstructed image by applying an output layer (e.g., output layer 916 of FIG. 9, sometimes referred to as a deconvolutional layer or a transposed convolutional layer) having dimensions "n×n". For example, applying the output layer to the output of the second convolutional layer may apply a predetermined number of filters (e.g., deconvolutional filters or transposed convolutional filters), each having predetermined dimensions and a predetermined stride, to the second convolutional layer. The dimensions of the filters applied by the output layer may be different from the dimensions of the filters applied by the first and second convolutional layers.

Figure 11:
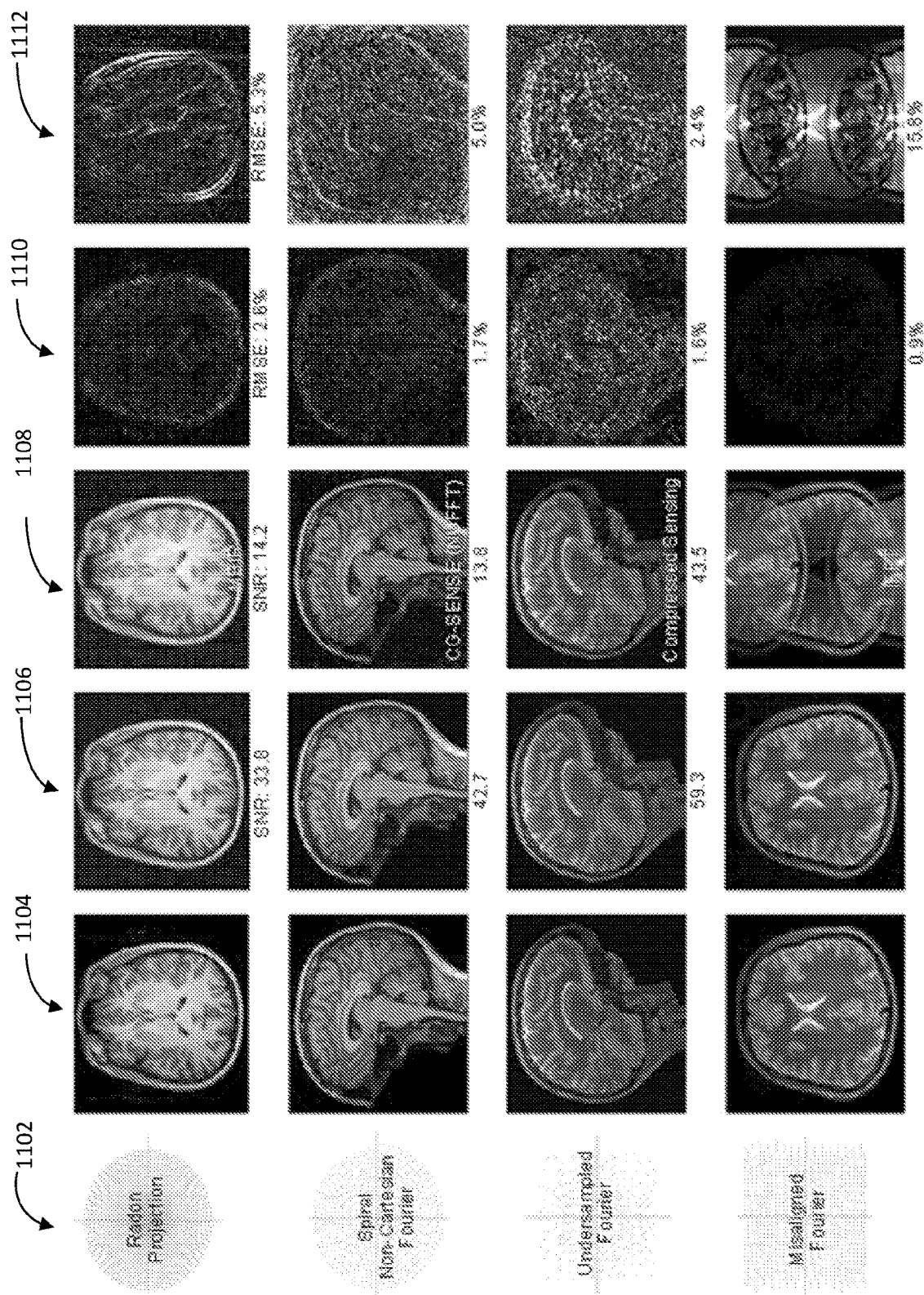
FIG. 11 shows an array of images that illustrates results of both data-driven manifold learning image reconstruction techniques and conventional techniques.

FIG. 11 shows illustrative comparisons between image reconstruction results using the data-driven manifold learning image reconstruction techniques described above in connection with FIGS. 8-10 and conventional techniques. Column 1102 illustrates different types of encoding that may effectively be applied to captured sensor data based on the acquisition method/imaging system. Each encoding type may correspond to a different sensor domain.

Radon projection encoding here refers to the encoding that may be intrinsically present in raw image data is captured using X-ray CT scanning or PET scanning medical imaging techniques. For example, conventional techniques such as filtered back projection reconstruction, adaptive statistical iterative reconstruction, and model-based iterative reconstruction (MBIR) may be applied to radon projection encoded data in order to transform the encoded data into the image domain.

Spiral non-Cartesian Fourier encoding here refers to encoding that may be intrinsically applied to raw image data produced when performing spiral or radial methods of MRI scanning. For example, conventional techniques such as the non-uniform fast Fourier transform (NUFFT) may be applied to spiral non-Cartesian Fourier encoded data in order to transform the encoded data into the image domain.

Under-sampled Fourier encoding here refers to encoding that may be intrinsically applied to raw image data produced when performing compressed sensing in magnetic resonance (MR) imaging. For example, conventional techniques such as compressed sensing reconstruction with wavelet sparsifying transforms may be applied to under-sampled Fourier encoded data in order to transform the encoded data into the image domain.

Misaligned Fourier encoding here refers to encoding that may be intrinsically applied to raw image data produced when performing MRI scanning that is affected by sampling distortion (e.g., as a result of miscalibrated hardware). For example, conventional techniques such as the inverse fast Fourier transform (IFFT) may be applied to the misaligned Fourier encoded data in order to transform the encoded data into the image domain.

Column 1104 includes reference images for each of the encoding types. Each reference image shows, respectively, what the encoded data should look like when correctly reconstructed (e.g., transformed) into the image domain. Each reference image may be converted to a respective one of the sensor domains corresponding to the associated encoding types of column 1102.

Column 1106 includes reconstructed images for each of the encoding types that were reconstructed using the AUTOMAP reconstruction techniques of the present disclosure (e.g., as described above in connection with FIGS. 8-10).

Column 1108 includes reconstructed images for each of the encoding types that were reconstructed using the conventional image reconstruction methods traditionally applied for those respective coding types. For example, for Radon projection encoded data, a MBIR reconstructed image is shown. For spiral non-Cartesian Fourier encoded data, a NUFFT reconstructed image is shown. For under-sampled Fourier encoded data, a compressed sensing reconstructed image is shown. For misaligned Fourier encoded data, an IFFT reconstructed image is shown.

Column 1110 includes neural network error images for each of the encoding types, representing the differences between the neural network reconstructed images of column 1106 and the reference images of column 1104.

Column 1112 includes conventional error images for each of the encoding types, representing the difference between the conventionally reconstructed images of column 1108 and the reference images of column 1104.

As shown, the neural network reconstructed images of column 1106 consistently have a higher signal-to-noise ratio (SNR) compared to that of the corresponding conventionally reconstructed images of column 1108. Additionally, the root mean square error (RMSE) of the neural network error images is shown here to be consistently lower than the corresponding conventional error images of column 1112. Thus, based on the examples shown here, neural network reconstruction techniques of the present disclosure may be considered advantageous over the corresponding conventional techniques of the illustrated examples due to their comparatively greater SNR and comparatively lower RMSE.

Using the data-driven manifold learning techniques described above, opposed to conventional data transformation techniques such as the Discrete Fourier Transform, the domain for signal acquisition may be comparatively more flexible and can be more tailored to the underlying physical system. This generalized reconstruction can compensate for hardware imperfections such as gradient nonlinearity in MRI by being trained on the system being used. These and other imaging artifacts can be compensated for by the trained neural network. Also, generalized reconstruction may have higher noise immunity and reduced undersampling error when appropriately trained, allowing for greatly accelerated image capture. Additionally, non-intuitive Pulse sequences (e.g., for MRI applications) may be generated by data-driven manifold learning because the signals can be acquired in a non-intuitive domain before reconstruction. Further, pulse sequences can be tailored in real-time in response to specific individual subjects or samples. Training may, for example, be performed with large public or private image databases (e.g. PACS, Human Connectome Project, etc.).

What is claimed is:

1. A medical imaging system comprising:
    an image sensor configured to acquire signal data from a patient, wherein the signal data is in a signal domain;
    a data-driven, manifold-learning, neural network configured to receive the signal data from the image sensor and to transform the signal data from the signal domain to an image domain to produce an image of the patient; and
    a display configured to display the image of the patient.

2. The medical imaging system of claim 1 wherein the image sensor includes at least one of:
    a radio frequency (RF) system of a magnetic resonance imaging (MRI) system and wherein the signal data comprises magnetic resonance data;
    an x-ray detector of a computed tomography (CT) system and wherein the signal data comprises x-ray attenuation data;
    a gamma ray detector of an emission tomography system and wherein the signal data comprises emission tomography data;
    an ultrasound transducer of an ultrasound system and wherein the signal data comprises ultrasound data; and
    an optical sensor of an optical imaging system and wherein the signal data comprises optical imaging data.

3. The system of claim 1, wherein the data-driven, manifold-learning, neural network includes an input layer connected to a first hidden layer.

4. The system of claim 3, wherein the first connected layer is an $n^2 \times 1$ first connected layer and the input layer is fully connected to the $n^2 \times 1$ first hidden layer.

5. The system of claim 4, wherein the $n^2 \times 1$ first hidden layer is activated by a non-linear activation function.

6. The system of claim 5, wherein the non-linear activation function is a hyperbolic tangent function.

7. The system of claim 5, wherein $n^2 \times 1$ first hidden layer is fully connected to a $n^2 \times 1$ second hidden layer, which produces a n×n matrix when applied to $n^2 \times 1$ first hidden layer.

8. The system of claim 7, wherein the data-driven, manifold-learning, neural network includes fully connected layers that represent affine mapping followed by an activation function.

9. The system of claim 8, wherein the activation function is given by $g(\chi)=s(W\chi+b)$ where $g(\chi)$ is a matrix resulting from the application of the $n^2 \times 1$ first hidden layer to the input layer $\chi$ where W is a $n^2 \times n^2$ weight matrix, where b is an offset vector of dimensionality $n^2$, and where s is the activation function.

10. A system comprising:
    an input configured to receive signal data in a signal domain from an image sensor configured to generate the signal data, wherein the signal data corresponds to a captured image; and
    a processor configured to implement a data-driven, manifold-learning, neural network configured to receive the signal data from the image sensor and to supply the signal data from the image sensor to the data-driven, manifold-learning, neural network to transform the signal data from the signal domain to an image domain to produce the captured image.

11. The system of claim 10, wherein the data-driven, manifold-learning, neural network is configured to transform the signal data from the signal domain to the image domain by:
    applying, a plurality of fully connected layers of the data-driven, manifold-learning, neural network to the signal data to produce a matrix.

12. The system of claim 11, wherein the plurality of fully connected layers comprises:
    a first hidden layer configured to operate on signal data using matrix multiplication followed by an activation function; and
    a second hidden layer configured to produce the matrix from the first hidden layer, wherein the matrix has dimensions corresponding to dimensions of the signal data.

13. The system of claim 12, wherein the plurality of fully connected layers further comprises:
    an input layer configured to separate real components of the signal data from imaginary components of the signal data and to concatenate the real components and the imaginary components to produce an input vector; and
    wherein the first hidden layer is applied to the input vector.

14. The system of claim 11, wherein the activation function is a hyperbolic tangent activation function.

15. The system of claim 11, wherein the data-driven, manifold-learning, neural network is further configured to transform the signal data from the signal domain to the image domain using the neural network by:

applying, with a plurality of convolutional layers of the neural network, a predetermined number of convolutional filters to the matrix.

16. The system of claim 15, wherein the data-driven, manifold-learning, neural network is further configured to transform the signal data from the signal domain to the image domain using the neural network by:
applying, with a deconvolutional layer of the neural network, a predetermined number of deconvolutional filters to a convolutional layer of the plurality of convolutional layers to produce image data in the image domain that corresponds to the captured image.

17. The system of claim 10, wherein the image sensor includes at least one of:
a radio frequency (RF) system of a magnetic resonance imaging (MRI) system and wherein the signal data comprises magnetic resonance data;
an x-ray detector of a computed tomography (CT) system and wherein the signal data comprises x-ray attenuation data;
a gamma ray detector of an emission tomography system and wherein the signal data comprises emission tomography data;
an ultrasound transducer of an ultrasound system and wherein the signal data comprises ultrasound data; and
an optical sensor of an optical imaging system and wherein the signal data comprises optical imaging data.

18. A method comprising:
generating, with an image sensor, signal data in a signal domain, wherein the signal data corresponds to a captured image;
receiving, with a processor, the signal data from the image sensor; and
executing, with the processor, a data-driven, manifold-learning, neural network for transforming the signal data from a signal domain to an image domain using a neural network to produce the captured image.

19. The method of claim 18, wherein executing the data-driven, manifold-learning, neural network for transforming the signal data from the signal domain to the image domain using the neural network comprises executing instructions for:
applying a plurality of fully connected layers of the data-driven, manifold-learning, neural network to the signal data to produce a matrix.

20. The method of claim 19, wherein applying the plurality of fully connected layers of the data data-driven, manifold-learning, neural network to the signal data to produce the matrix comprises:
separating, at an input layer of the plurality of fully connected layers, real components of the signal data from imaginary components of the signal data;
concatenating, at the input layer, the real components and the imaginary components to produce an input vector,
applying a first hidden layer of a plurality of fully connected layers to the input vector, and
producing, with a second hidden layer of the plurality of fully connected layers, the matrix from the first hidden layer, wherein the matrix has dimensions corresponding to dimensions of the signal data.

21. The method of claim 19, wherein applying the first hidden layer of the plurality of fully connected layers to the input vector comprises performing matrix multiplication on the input vector before applying a hyperbolic tangent activation function.

22. The method of claim 19, wherein executing instructions for transforming the signal data from the signal domain to the image domain using the data-driven, manifold-learning, neural network further comprises executing instructions for:
applying, with a plurality of convolutional layers of the data-driven, manifold-learning, neural network, a predetermined number of convolutional filters to the matrix.

23. The method of claim 22, wherein executing instructions for transforming the signal data from the signal domain to the image domain using the data-driven, manifold-learning, neural network further comprises executing instructions for:
applying, with a deconvolutional layer of the data-driven, manifold-learning, neural network, a predetermined number of deconvolutional filters to a convolutional layer of the plurality of convolutional layers to produce image data in the image domain that corresponds to the captured image.

24. The method of claim 18, wherein generating the signal data comprises:
applying, with a magnetic resonance imaging system, a magnetic resonance pulse sequence to a sample;
detecting, with the magnetic resonance imaging system, responsive magnetic resonance signals generated by the sample in response to the magnetic resonance pulse sequence; and
sampling the responsive magnetic resonance signals to generate the signal data.

25. A system comprising:
a processor configured to implement a data-driven, manifold-learning, neural network for transforming signal data from a first domain to a second domain to produce an image by:
processing data using the data-driven, manifold-learning, neural network to produce the image; and
wherein the first domain is a signal domain and the second domain is an image domain.

26. The system of claim 25, wherein processing the signal data using the data-driven, manifold-learning, neural network comprises:
applying a plurality of fully connected layers of the data-driven, manifold-learning, neural network to the signal data to produce a matrix.

27. The system of claim 26, wherein the plurality of fully connected layers comprises:
an input layer configured to separate real components of the signal data from imaginary components of the signal data and to concatenate the real components and the imaginary components to produce an input vector;
a first hidden layer configured to operate on the input vector using matrix multiplication followed by an activation function; and
a second hidden layer configured to produce the matrix from the first hidden layer, wherein the matrix has dimensions corresponding to dimensions of the signal data.

28. The system of claim 26, wherein the activation function is a hyperbolic tangent activation function.

29. The system of claim 26, wherein processing the signal data using the data-driven, manifold-learning, neural network further comprises:
applying, with a plurality of convolutional layers of the data-driven, manifold-learning, neural network, a predetermined number of convolutional filters to the matrix.

30. The system of claim 29, wherein processing the signal data using the data-driven, manifold-learning, neural network neural network further comprises:

applying, with a deconvolutional layer of the neural network, a predetermined number of deconvolutional filters to a convolutional layer of the plurality of convolutional layers to produce transformed data in the second domain.

* * * * *

UNITED STATES PATENT AND TRADEMARK OFFICE
CERTIFICATE OF CORRECTION

PATENT NO. : 11,620,772 B2
APPLICATION NO. : 16/326910
DATED : April 4, 2023
INVENTOR(S) : Matthew S. Rosen et al.

It is certified that error appears in the above-identified patent and that said Letters Patent is hereby corrected as shown below:

In the Specification

Column 20, Line 3, "where is" should be --where $x$ is--.

In the Claims

Column 25, Claim 20, Line 47, "the data data-driven" should be --the data-driven--.

Signed and Sealed this
Sixteenth Day of May, 2023

Katherine Kelly Vidal
*Director of the United States Patent and Trademark Office*